(12) United States Patent
Shaw et al.

(10) Patent No.: US 7,314,756 B2
(45) Date of Patent: Jan. 1, 2008

(54) PLANT TUBBY-LIKE PROTEINS

(75) Inventors: Jei-Fu Shaw, Taipei (TW); Chia-Ping Lai, Taipei (TW)

(73) Assignee: Academia Sininca, Taipei (TW)

(*) Notice: Subject to any disclaimer, the term of this patent is extended or adjusted under 35 U.S.C. 154(b) by 242 days.

(21) Appl. No.: 10/763,042

(22) Filed: Jan. 21, 2004

(65) Prior Publication Data

US 2005/0014266 A1  Jan. 20, 2005

Related U.S. Application Data

(60) Provisional application No. 60/441,380, filed on Jan. 21, 2003.

(51) Int. Cl.
- *A01H 5/00* (2006.01)
- *C12N 15/82* (2006.01)
- *C12N 15/87* (2006.01)
- *C12N 5/14* (2006.01)

(52) U.S. Cl. .................. 435/468; 435/320.1; 435/419; 800/289; 800/295; 536/23.6

(58) Field of Classification Search ................ None
See application file for complete search history.

(56) References Cited

OTHER PUBLICATIONS

Lin et al. (NCBI, GenBank, Sequence Accession No. AC011623, pp. 1-37, Published Oct. 2002).*
Maniatis et al. (Cold Spring Harbor Laboratory, Chapter 12, pp. 404-421, New York, 1982).*
Lin et al. (NCBI, GenBank, Sequence Accession No. AC011623, pp. 1-37, Published Nov. 1999, updated in Jan. 2001).*
Sandra Santagata et al. "G-Protein Signaling Through Tubby Proteins". Science 292:2041-2050, Jun. 15, 2001.
Charles A. Lewis et al. "Tubby-like Protein 1 Homozygous Splice-Site Mutation Causes Early-Onset Severe Retinal Degeneration". Invest Ophthalmol Vis Sci 40:2106-2114, 1999.
Jennifer M. Gagne et al. "The F-box subunit of the SCF E3 complex is encoded by a diverse superfamily of genes in *Arabidopsis*". PNAS 99(17):11519-11524, Aug. 20, 2002.
Titus J. Boggon et al. "Implication of Tubby Proteins as Transcriptional Factors by Structure-Based Functional Analysis". Science 286:2119-2125, Dec. 10, 1999.
Michael A. North et al. "Molecular characterization of *TUB, TULP1*, and *TULP2*, members of the novel tubby gene family and their possible relation to ocular diseases". Proc. Natl. Acad. Sci. USA 94:3128-3133, Apr. 1997.
Patrick W. Kleyn et al. "Identification and Characterization of the Mouse Obesity Gene *tubby*: A member of a novel gene family". Cell 85:281-290, Apr. 19, 1996.
Sakae Ikeda et al. "Cell-Specific Expression of Tubby Gene Family Members *Tub, Tulp1, 2, and 3*) in the Retina". Invest Ophthalmol Vis Sci 40:2706-2712, 1999.
Akihiro Ikeda et al. "The tubby-like proteins, a family with roles in neuronal development and function". Journal of Cell Science 115:9-14, 2002.
Patsy M. Nishina et al. "Molecular chracterization of a novel tubby gene family member, TULP3, in the mouse and humans". Genomics 54:215-220, 1998.

* cited by examiner

*Primary Examiner*—Phuong T Bui
*Assistant Examiner*—Vinod Kumar
(74) *Attorney, Agent, or Firm*—Occhiuti Rohlicek & Tsao LLP

(57) ABSTRACT

An isolated polypeptide containing an amino acid sequence at least 70% identical to SEQ ID NO: 1, 2, 3, 4, 5, 6, 7, 8, 9, 10, or 11, and an isolated nucleic acid encoding the polypeptide are disclosed. Disclosed is an isolated nucleic acid that, under stringent conditions, hybridizes to a probe containing SEQ ID NO:20; or its complementary sequence. Also disclosed are (1) a transformed cell or a transgenic plant containing such a nucleic acid and (2) a transformed cell or a transgenic plant lacking the polypeptide encoded by the nucleic acid. Also within the scope of the invention are methods for making the transformed cells or transgenic plants.

7 Claims, No Drawings

SEQUENCE LISTING

<160> NUMBER OF SEQ ID NOS: 48

<210> SEQ ID NO 1
<211> LENGTH: 450
<212> TYPE: PRT
<213> ORGANISM: Arabidopsis sp.

<400> SEQUENCE: 1

```
Met Ser Phe Arg Ser Ile Val Arg Asp Val Arg Asp Ser Ile Gly Ser
1               5                   10                  15

Leu Ser Arg Arg Ser Phe Asp Phe Lys Leu Ser Ser Leu Asn Lys Glu
            20                  25                  30

Gly Gly Lys Ser Arg Gly Ser Val Gln Asp Ser His Glu Glu Gln Leu
        35                  40                  45

Val Val Thr Ile Gln Glu Thr Pro Trp Ala Asn Leu Pro Pro Glu Leu
    50                  55                  60

Leu Arg Asp Val Ile Lys Arg Leu Glu Glu Ser Glu Ser Val Trp Pro
65                  70                  75                  80

Ala Arg Arg His Val Val Ala Cys Ala Ser Val Cys Arg Ser Trp Arg
                85                  90                  95
```

```
Asp Met Cys Lys Glu Ile Val Gln Ser Pro Glu Leu Ser Gly Lys Ile
            100                 105                 110

Thr Phe Pro Val Ser Leu Lys Gln Pro Gly Pro Arg Asp Ala Thr Met
            115                 120                 125

Gln Cys Phe Ile Lys Arg Asp Lys Ser Asn Leu Thr Tyr His Leu Tyr
    130                 135                 140

Leu Cys Leu Ser Pro Ala Leu Leu Val Glu Asn Gly Lys Phe Leu Leu
145                 150                 155                 160

Ser Ala Lys Arg Ile Arg Arg Thr Thr Tyr Thr Glu Tyr Val Ile Ser
                165                 170                 175

Met His Ala Asp Thr Ile Ser Arg Ser Ser Asn Thr Tyr Ile Gly Lys
            180                 185                 190

Ile Arg Ser Asn Phe Leu Gly Thr Lys Phe Ile Ile Tyr Asp Thr Gln
        195                 200                 205

Pro Ala Tyr Asn Ser Asn Ile Ala Arg Ala Val Gln Pro Val Gly Leu
        210                 215                 220

Ser Arg Arg Phe Tyr Ser Lys Arg Val Ser Pro Lys Val Pro Ser Gly
225                 230                 235                 240

Ser Tyr Lys Ile Ala Gln Val Ser Tyr Glu Leu Asn Val Leu Gly Thr
                245                 250                 255

Arg Gly Pro Arg Arg Met His Cys Ala Met Asn Ser Ile Pro Ala Ser
            260                 265                 270

Ser Leu Ala Glu Gly Gly Thr Val Pro Gly Gln Pro Asp Ile Ile Val
            275                 280                 285

Pro Arg Ser Ile Leu Asp Glu Ser Phe Arg Ser Ile Thr Ser Ser Ser
        290                 295                 300

Ser Arg Lys Ile Thr Tyr Asp Tyr Ser Asn Asp Phe Ser Ser Ala Arg
305                 310                 315                 320

Phe Ser Asp Ile Leu Gly Pro Leu Ser Glu Asp Gln Glu Val Val Leu
                325                 330                 335

Glu Glu Gly Lys Glu Arg Asn Ser Pro Pro Leu Val Leu Lys Asn Lys
            340                 345                 350

Pro Pro Arg Trp His Glu Gln Leu Gln Cys Trp Cys Leu Asn Phe Arg
            355                 360                 365

Gly Arg Val Thr Val Ala Ser Val Lys Asn Phe Gln Leu Ile Ala Ala
    370                 375                 380

Asn Gln Pro Gln Pro Gln Pro Gln Pro Gln Pro Gln Pro Gln Pro Leu
385                 390                 395                 400

Thr Gln Pro Gln Pro Ser Gly Gln Thr Asp Gly Pro Asp Lys Ile Ile
                405                 410                 415

Leu Gln Phe Gly Lys Val Gly Lys Asp Met Phe Thr Met Asp Phe Arg
            420                 425                 430

Tyr Pro Leu Ser Ala Phe Gln Ala Phe Ala Ile Cys Leu Ser Ser Phe
            435                 440                 445

Asp Thr
    450

<210> SEQ ID NO 2
<211> LENGTH: 394
<212> TYPE: PRT
<213> ORGANISM: Arabidopsis sp.

<400> SEQUENCE: 2

Met Ser Leu Lys Ser Ile Leu Arg Asp Leu Lys Glu Val Arg Asp Gly
1               5                   10                  15
```

```
Leu Gly Gly Ile Ser Lys Arg Ser Trp Ser Lys Ser His Ile Ala
         20                  25                  30

Pro Asp Gln Thr Thr Pro Leu Asp Asn Ile Pro Gln Ser Pro Trp
         35                  40                  45

Ala Ser Leu Pro Pro Glu Leu Leu His Asp Ile Ile Trp Arg Val Glu
 50                  55                  60

Glu Ser Glu Thr Ala Trp Pro Ala Arg Ala Ala Val Val Ser Cys Ala
 65                  70                  75                  80

Ser Val Cys Lys Ser Trp Arg Gly Ile Thr Met Glu Ile Val Arg Ile
                 85                  90                  95

Pro Glu Gln Cys Gly Lys Leu Thr Phe Pro Ile Ser Leu Lys Gln Pro
             100                 105                 110

Gly Pro Arg Asp Ser Pro Ile Gln Cys Phe Ile Lys Arg Asn Arg Ala
         115                 120                 125

Thr Ala Thr Tyr Ile Leu Tyr Tyr Gly Leu Met Pro Ser Glu Thr Glu
         130                 135                 140

Asn Asp Lys Leu Leu Leu Ala Ala Arg Arg Ile Arg Arg Ala Thr Cys
145                 150                 155                 160

Thr Asp Phe Ile Ile Ser Leu Ser Ala Lys Asn Phe Ser Arg Ser Ser
                 165                 170                 175

Ser Thr Tyr Val Gly Lys Leu Arg Ser Gly Phe Leu Gly Thr Lys Phe
             180                 185                 190

Thr Ile Tyr Asp Asn Gln Thr Ala Ser Ser Thr Ala Gln Ala Gln Pro
         195                 200                 205

Asn Arg Arg Leu His Pro Lys Gln Ala Ala Pro Lys Leu Pro Thr Asn
210                 215                 220

Ser Ser Thr Val Gly Asn Ile Thr Tyr Glu Leu Asn Val Leu Arg Thr
225                 230                 235                 240

Arg Gly Pro Arg Arg Met His Cys Ala Met Asp Ser Ile Pro Leu Ser
                 245                 250                 255

Ser Val Ile Ala Glu Pro Ser Val Val Gln Gly Ile Glu Glu Glu Val
             260                 265                 270

Ser Ser Ser Pro Ser Pro Lys Gly Glu Thr Ile Thr Thr Asp Lys Glu
         275                 280                 285

Ile Pro Asp Asn Ser Pro Ser Leu Arg Asp Gln Pro Leu Val Leu Lys
         290                 295                 300

Asn Lys Ser Pro Arg Trp His Glu Gln Leu Gln Cys Trp Cys Leu Asn
305                 310                 315                 320

Phe Lys Gly Arg Val Thr Val Ala Ser Val Lys Asn Phe Gln Leu Val
                 325                 330                 335

Ala Glu Ile Asp Ala Ser Leu Asp Ala Pro Pro Glu Glu His Glu Arg
             340                 345                 350

Val Ile Leu Gln Phe Gly Lys Ile Gly Lys Asp Ile Phe Thr Met Asp
         355                 360                 365

Tyr Arg Tyr Pro Leu Ser Ala Phe Gln Ala Phe Ala Ile Cys Ile Ser
         370                 375                 380

Ser Phe Asp Thr Lys Pro Ala Cys Glu Gly
385                 390

<210> SEQ ID NO 3
<211> LENGTH: 406
<212> TYPE: PRT
<213> ORGANISM: Arabidopsis sp.
```

<400> SEQUENCE: 3

```
Met Ser Phe Lys Ser Leu Ile Gln Asp Met Arg Gly Glu Leu Gly Ser
  1               5                  10                  15
Ile Ser Arg Lys Gly Phe Asp Val Arg Phe Gly Tyr Gly Arg Ser Arg
             20                  25                  30
Ser Gln Arg Val Val Gln Asp Thr Ser Val Pro Val Asp Ala Phe Lys
         35                  40                  45
Gln Ser Cys Trp Ala Ser Met Pro Pro Glu Leu Leu Arg Asp Val Leu
     50                  55                  60
Met Arg Ile Glu Gln Ser Glu Asp Thr Trp Pro Ser Arg Lys Asn Val
 65                  70                  75                  80
Val Ser Cys Ala Gly Val Cys Arg Asn Trp Arg Glu Ile Val Lys Glu
                 85                  90                  95
Ile Val Arg Val Pro Glu Leu Ser Ser Lys Leu Thr Phe Pro Ile Ser
            100                 105                 110
Leu Lys Gln Pro Gly Pro Arg Gly Ser Leu Val Gln Cys Tyr Ile Met
        115                 120                 125
Arg Asn Arg Ser Asn Gln Thr Tyr Tyr Leu Tyr Leu Gly Leu Asn Gln
130                 135                 140
Ala Ala Ser Asn Asp Asp Gly Lys Phe Leu Leu Ala Ala Lys Arg Phe
145                 150                 155                 160
Arg Arg Pro Thr Cys Thr Asp Tyr Ile Ile Ser Leu Asn Cys Asp Asp
                165                 170                 175
Val Ser Arg Gly Ser Asn Thr Tyr Ile Gly Lys Leu Arg Ser Asn Phe
            180                 185                 190
Leu Gly Thr Lys Phe Thr Val Tyr Asp Ala Gln Pro Thr Asn Pro Gly
        195                 200                 205
Thr Gln Val Thr Arg Thr Arg Ser Ser Arg Leu Leu Ser Leu Lys Gln
    210                 215                 220
Val Ser Pro Arg Ile Pro Ser Gly Asn Tyr Pro Val Ala His Ile Ser
225                 230                 235                 240
Tyr Glu Leu Asn Val Leu Gly Ser Arg Gly Pro Arg Arg Met Gln Cys
                245                 250                 255
Val Met Asp Ala Ile Pro Ala Ser Ala Val Glu Pro Gly Gly Thr Ala
            260                 265                 270
Pro Thr Gln Thr Glu Leu Val His Ser Asn Leu Asp Ser Phe Pro Ser
        275                 280                 285
Phe Ser Phe Phe Arg Ser Lys Ser Ile Arg Ala Glu Ser Leu Pro Ser
    290                 295                 300
Gly Pro Ser Ser Ala Ala Gln Lys Glu Gly Leu Leu Val Leu Lys Asn
305                 310                 315                 320
Lys Ala Pro Arg Trp His Glu Gln Leu Gln Cys Trp Cys Leu Asn Phe
                325                 330                 335
Asn Gly Arg Val Thr Val Ala Ser Val Lys Asn Phe Gln Leu Val Ala
            340                 345                 350
Ala Pro Glu Asn Gly Pro Ala Gly Pro Glu His Glu Asn Val Ile Leu
        355                 360                 365
Gln Phe Gly Lys Val Gly Lys Asp Val Phe Thr Met Asp Tyr Gln Tyr
    370                 375                 380
Pro Ile Ser Ala Phe Gln Ala Phe Thr Ile Cys Leu Ser Ser Phe Asp
385                 390                 395                 400
Thr Lys Ile Ala Cys Glu
                405
```

<210> SEQ ID NO 4
<211> LENGTH: 265
<212> TYPE: PRT
<213> ORGANISM: Arabidopsis sp.

<400> SEQUENCE: 4

Met Pro Pro Glu Leu Leu Arg Asp Val Leu Met Arg Ile Glu Arg Ser
 1               5                  10                  15

Glu Asp Thr Trp Pro Ser Arg Lys Asn Val Val Ser Cys Val Gly Val
            20                  25                  30

Cys Lys Asn Trp Arg Gln Ile Phe Lys Glu Ile Val Asn Val Pro Glu
        35                  40                  45

Val Ser Ser Lys Phe Thr Phe Pro Ile Ser Leu Lys Gln Pro Gly Pro
    50                  55                  60

Gly Gly Ser Leu Val Gln Cys Tyr Val Lys Arg Asn Arg Ser Asn Gln
65                  70                  75                  80

Thr Phe Tyr Leu Tyr Leu Gly Gly Glu Ala Lys Ile Phe Cys Gln Ser
                85                  90                  95

Glu Pro Ser Asp Ile Tyr Leu Val Pro Tyr Ser Tyr Arg Glu Thr His
            100                 105                 110

Cys Val Met Asp Ala Ile Ser Ala Ser Ala Val Lys Pro Gly Gly Thr
        115                 120                 125

Ala Thr Thr Gln Thr Glu Leu Asp Asn Phe Val Ser Phe Arg Ser Pro
    130                 135                 140

Ser Gly Gln Lys Glu Gly Val Leu Val Leu Lys Ser Lys Val Pro Arg
145                 150                 155                 160

Leu Glu Glu Gln Ser Trp Cys Leu Asp Phe Asn Gly Ser Pro Glu Asn
                165                 170                 175

Glu Pro Glu Asn Glu Asn Asp Ile Phe Gln Phe Ala Lys Val Gly Asn
            180                 185                 190

Leu His Lys Leu Phe Ser Leu Tyr Glu Ala Glu Trp Ile Pro Leu Val
        195                 200                 205

Arg Thr Ser Val Phe Ala Val Ile Ala Arg Val Cys Arg Asp Lys Lys
    210                 215                 220

His Thr Pro Ser Tyr Glu Leu Lys Leu Ala Leu Tyr Phe Ala Lys Asn
225                 230                 235                 240

Ser Ala Ile Leu Lys Lys Phe Val Leu Arg Gly Tyr Thr Arg Glu Glu
                245                 250                 255

Asp Leu Leu Ala Leu Pro Val Ala Asn
            260                 265

<210> SEQ ID NO 5
<211> LENGTH: 429
<212> TYPE: PRT
<213> ORGANISM: Arabidopsis sp.

<400> SEQUENCE: 5

Met Ser Phe Leu Ser Ile Val Arg Asp Val Arg Asp Thr Val Gly Ser
 1               5                  10                  15

Phe Ser Arg Arg Ser Phe Asp Val Arg Val Ser Asn Gly Thr Thr His
            20                  25                  30

Gln Arg Ser Lys Ser His Gly Val Glu Ala His Ile Glu Asp Leu Ile
        35                  40                  45

Val Ile Lys Asn Thr Arg Trp Ala Asn Leu Pro Ala Ala Leu Leu Arg
    50                  55                  60

```
Asp Val Met Lys Lys Leu Asp Glu Ser Glu Ser Thr Trp Pro Ala Arg
 65                  70                  75                  80

Lys Gln Val Val Ala Cys Ala Gly Val Cys Lys Thr Trp Arg Leu Met
                 85                  90                  95

Cys Lys Asp Ile Val Lys Ser Pro Glu Phe Ser Gly Lys Leu Thr Phe
            100                 105                 110

Pro Val Ser Leu Lys Gln Pro Gly Pro Arg Asp Gly Ile Ile Gln Cys
        115                 120                 125

Tyr Ile Lys Arg Asp Lys Ser Asn Met Thr Tyr His Leu Tyr Leu Ser
    130                 135                 140

Leu Ser Pro Ala Ile Leu Val Glu Ser Gly Lys Phe Leu Leu Ser Ala
145                 150                 155                 160

Lys Arg Ser Arg Arg Ala Thr Tyr Thr Glu Tyr Val Ile Ser Met Asp
                165                 170                 175

Ala Asp Asn Ile Ser Arg Ser Ser Thr Tyr Ile Gly Lys Leu Lys
            180                 185                 190

Ser Asn Phe Leu Gly Thr Lys Phe Ile Val Tyr Asp Thr Ala Pro Ala
        195                 200                 205

Tyr Asn Ser Ser Gln Ile Leu Ser Pro Pro Asn Arg Ser Arg Ser Phe
    210                 215                 220

Asn Ser Lys Lys Val Ser Pro Lys Val Pro Ser Gly Ser Tyr Asn Ile
225                 230                 235                 240

Ala Gln Val Thr Tyr Glu Leu Asn Leu Leu Gly Thr Arg Gly Pro Arg
                245                 250                 255

Arg Met Asn Cys Ile Met His Ser Ile Pro Ser Leu Ala Leu Glu Pro
            260                 265                 270

Gly Gly Thr Val Pro Ser Gln Pro Glu Phe Leu Gln Arg Ser Leu Asp
        275                 280                 285

Glu Ser Phe Arg Ser Ile Gly Ser Ser Lys Ile Val Asn His Ser Gly
    290                 295                 300

Asp Phe Thr Arg Pro Lys Glu Glu Gly Lys Val Arg Pro Leu Val
305                 310                 315                 320

Leu Lys Thr Lys Pro Pro Arg Trp Leu Gln Pro Leu Arg Cys Trp Cys
                325                 330                 335

Leu Asn Phe Lys Gly Arg Val Thr Val Ala Ser Val Lys Asn Phe Gln
            340                 345                 350

Leu Met Ser Ala Ala Thr Val Gln Pro Gly Ser Gly Ser Asp Gly Gly
        355                 360                 365

Ala Leu Ala Thr Arg Pro Ser Leu Ser Pro Gln Gln Pro Glu Gln Ser
    370                 375                 380

Asn His Asp Lys Ile Ile Leu His Phe Gly Lys Val Gly Lys Asp Met
385                 390                 395                 400

Phe Thr Met Asp Tyr Arg Tyr Pro Leu Ser Ala Phe Gln Ala Phe Ala
                405                 410                 415

Ile Ser Leu Ser Thr Phe Asp Thr Lys Leu Ala Cys Glu
            420                 425

<210> SEQ ID NO 6
<211> LENGTH: 388
<212> TYPE: PRT
<213> ORGANISM: Arabidopsis sp.

<400> SEQUENCE: 6

Met Ser Leu Lys Asn Ile Val Lys Asn Lys Tyr Lys Ala Ile Gly Arg
```

```
              1               5                  10                 15
Arg Gly Arg Ser His Ile Ala Pro Glu Gly Ser Ser Val Ser Ser Ser
                    20                 25                 30

Leu Ser Thr Asn Glu Gly Leu Asn Gln Ser Ile Trp Val Asp Leu Pro
            35                  40                 45

Pro Glu Leu Leu Leu Asp Ile Ile Gln Arg Ile Glu Ser Glu Gln Ser
            50                  55                 60

Leu Trp Pro Gly Arg Arg Asp Val Val Ala Cys Ala Ser Val Cys Lys
65                      70                  75                  80

Ser Trp Arg Glu Met Thr Lys Glu Val Lys Val Pro Glu Leu Ser
                    85                  90                 95

Gly Leu Ile Thr Phe Pro Ile Ser Leu Arg Gln Pro Gly Pro Arg Asp
                    100                105                110

Ala Pro Ile Gln Cys Phe Ile Lys Arg Glu Arg Ala Thr Gly Ile Tyr
            115                 120                125

Arg Leu Tyr Leu Gly Leu Ser Pro Ala Leu Ser Gly Asp Lys Ser Lys
            130                 135                140

Leu Leu Leu Ser Ala Lys Arg Val Arg Arg Ala Thr Gly Ala Glu Phe
145                     150                 155                 160

Val Val Ser Leu Ser Gly Asn Asp Phe Ser Arg Ser Ser Asn Tyr
                    165                 170                 175

Ile Gly Lys Leu Arg Ser Asn Phe Leu Gly Thr Lys Phe Thr Val Tyr
                    180                 185                 190

Glu Asn Gln Pro Pro Pro Phe Asn Arg Lys Leu Pro Pro Ser Met Gln
                    195                 200                 205

Val Ser Pro Trp Val Ser Ser Ser Ser Ser Tyr Asn Ile Ala Ser
            210                 215                 220

Ile Leu Tyr Glu Leu Asn Val Leu Arg Thr Arg Gly Pro Arg Arg Met
225                     230                 235                 240

Gln Cys Ile Met His Ser Ile Pro Ile Ser Ala Ile Gln Glu Gly Gly
                    245                 250                 255

Lys Ile Gln Ser Pro Thr Glu Phe Thr Asn Gln Gly Lys Lys Lys Lys
                    260                 265                 270

Lys Pro Leu Met Asp Phe Cys Ser Gly Asn Leu Gly Gly Glu Ser Val
            275                 280                 285

Ile Lys Glu Pro Leu Ile Leu Lys Asn Lys Ser Pro Arg Trp His Glu
            290                 295                 300

Gln Leu Gln Cys Trp Cys Leu Asn Phe Lys Gly Arg Val Thr Val Ala
305                     310                 315                 320

Ser Val Lys Asn Phe Gln Leu Val Ala Ala Ala Glu Ala Gly Lys
                    325                 330                 335

Asn Met Asn Ile Pro Glu Glu Glu Gln Asp Arg Val Ile Leu Gln Phe
                    340                 345                 350

Gly Lys Ile Gly Lys Asp Ile Phe Thr Met Asp Tyr Arg Tyr Pro Ile
                    355                 360                 365

Ser Ala Phe Gln Ala Phe Ala Ile Cys Leu Ser Ser Phe Asp Thr Lys
            370                 375                 380

Pro Val Cys Glu
385

<210> SEQ ID NO 7
<211> LENGTH: 379
<212> TYPE: PRT
<213> ORGANISM: Arabidopsis sp.
```

<400> SEQUENCE: 7

```
Met Pro Leu Ser Arg Ser Leu Leu Ser Arg Ile Ser Asn Ser Phe
1               5                   10                  15

Arg Phe His Gln Gly Glu Thr Thr Ala Pro Glu Ser Glu Ser Ile
            20                  25                  30

Pro Pro Pro Ser Asn Met Ala Gly Ser Ser Trp Ser Ala Met Leu
        35                  40                  45

Pro Glu Leu Leu Gly Glu Ile Ile Arg Arg Val Glu Glu Thr Glu Asp
    50                  55                  60

Arg Trp Pro Gln Arg Arg Asp Val Val Thr Cys Ala Cys Val Ser Lys
65                  70                  75                  80

Lys Trp Arg Glu Ile Thr His Asp Phe Ala Arg Ser Ser Leu Asn Ser
                85                  90                  95

Gly Lys Ile Thr Phe Pro Ser Cys Leu Lys Leu Pro Gly Pro Arg Asp
            100                 105                 110

Phe Ser Asn Gln Cys Leu Ile Lys Arg Asn Lys Lys Thr Ser Thr Phe
            115                 120                 125

Tyr Leu Tyr Leu Ala Leu Thr Pro Ser Phe Thr Asp Lys Gly Lys Phe
    130                 135                 140

Leu Leu Ala Ala Arg Arg Phe Arg Thr Gly Ala Tyr Thr Glu Tyr Ile
145                 150                 155                 160

Ile Ser Leu Asp Ala Asp Asp Phe Ser Gln Gly Ser Asn Ala Tyr Val
                165                 170                 175

Gly Lys Leu Arg Ser Asp Phe Leu Gly Thr Asn Phe Thr Val Tyr Asp
            180                 185                 190

Ser Gln Pro Pro His Asn Gly Ala Lys Pro Ser Asn Gly Lys Ala Ser
    195                 200                 205

Arg Arg Phe Ala Ser Lys Gln Ile Ser Pro Gln Val Pro Ala Gly Asn
210                 215                 220

Phe Glu Val Gly His Val Ser Tyr Lys Phe Asn Leu Leu Lys Ser Arg
225                 230                 235                 240

Gly Pro Arg Arg Met Val Ser Thr Leu Arg Cys Pro Ser Pro Ser Pro
                245                 250                 255

Ser Ser Ser Ser Ala Gly Leu Ser Ser Asp Gln Lys Pro Cys Asp Val
            260                 265                 270

Thr Lys Ile Met Lys Lys Pro Asn Lys Asp Gly Ser Ser Leu Thr Ile
    275                 280                 285

Leu Lys Asn Lys Ala Pro Arg Trp His Glu His Leu Gln Cys Trp Cys
290                 295                 300

Leu Asn Phe His Gly Arg Val Thr Val Ala Ser Val Lys Asn Phe Gln
305                 310                 315                 320

Leu Val Ala Thr Val Asp Gln Ser Gln Pro Ser Gly Lys Gly Asp Glu
                325                 330                 335

Glu Thr Val Leu Leu Gln Phe Gly Lys Val Gly Asp Asp Thr Phe Thr
            340                 345                 350

Met Asp Tyr Arg Gln Pro Leu Ser Ala Phe Gln Ala Phe Ala Ile Cys
    355                 360                 365

Leu Thr Ser Phe Gly Thr Lys Leu Ala Cys Glu
    370                 375
```

<210> SEQ ID NO 8
<211> LENGTH: 397
<212> TYPE: PRT

<213> ORGANISM: Arabidopsis sp.

<400> SEQUENCE: 8

```
Met Ala Gly Ser Arg Lys Val Asn Asp Leu Leu Glu Asn Lys Gly
  1               5                  10                  15
Asn Val Asp Thr Ile Thr Gly Ser Leu Ser Thr Gln Lys Gly Glu Asp
             20                  25                  30
Lys Glu Asn Val Ser Pro Glu Lys Val Ser Thr Val Glu Thr Arg
         35                  40                  45
Lys Leu Asp Arg Ala Leu Lys Ser Gln Ser Met Lys Gly Asn Ser Gly
 50                  55                  60
Phe Pro Thr Glu Val Thr Asn Phe Lys Ser Phe Ser Thr Gly Gly Arg
 65                  70                  75                  80
Thr Ala Leu Lys Gln Ser Ser Leu Gln Ala Cys Met Gln Lys Asn Ser
                 85                  90                  95
Glu Val Asp Lys Ser Ser Phe Gly Met Lys Thr Trp Thr Ser Val Asp
            100                 105                 110
Ser Glu His Ser Ser Ser Leu Lys Val Trp Glu Phe Ser Asp Ser Glu
            115                 120                 125
Ala Ala Pro Ala Ser Ser Trp Ser Thr Leu Pro Asn Arg Ala Leu Leu
        130                 135                 140
Cys Lys Thr Leu Pro Leu Asp Val Gly Arg Cys Thr Cys Leu Ile Val
145                 150                 155                 160
Lys Glu Gln Ser Pro Glu Gly Leu Ser His Gly Ser Val Tyr Ser Leu
                165                 170                 175
Tyr Thr His Glu Gly Arg Gly Arg Lys Asp Arg Lys Leu Ala Val Ala
            180                 185                 190
Tyr His Ser Arg Arg Asn Gly Lys Ser Ile Phe Arg Val Ala Gln Asn
        195                 200                 205
Val Lys Gly Leu Leu Cys Ser Ser Asp Glu Ser Tyr Val Gly Ser Met
    210                 215                 220
Thr Ala Asn Leu Leu Gly Ser Lys Tyr Tyr Ile Trp Asp Lys Gly Val
225                 230                 235                 240
Arg Val Gly Ser Val Gly Lys Met Val Lys Pro Leu Leu Ser Val Val
                245                 250                 255
Ile Phe Thr Pro Thr Ile Thr Thr Trp Thr Gly Ser Tyr Arg Arg Met
            260                 265                 270
Arg Thr Leu Leu Pro Lys Gln Gln Pro Met Gln Lys Asn Asn Asn Lys
        275                 280                 285
Gln Val Gln Gln Ala Ser Lys Leu Pro Leu Asp Trp Leu Glu Asn Lys
    290                 295                 300
Glu Lys Ile Gln Lys Leu Cys Ser Arg Ile Pro His Tyr Asn Lys Ile
305                 310                 315                 320
Ser Lys Gln His Glu Leu Asp Phe Arg Asp Arg Gly Arg Thr Gly Leu
                325                 330                 335
Arg Ile Gln Ser Ser Val Lys Asn Phe Gln Leu Thr Leu Thr Glu Thr
            340                 345                 350
Pro Arg Gln Thr Ile Leu Gln Met Gly Arg Val Asp Lys Ala Arg Tyr
        355                 360                 365
Val Ile Asp Phe Arg Tyr Pro Phe Ser Gly Tyr Gln Ala Phe Cys Ile
    370                 375                 380
Cys Leu Ala Ser Ile Asp Ser Lys Leu Cys Cys Thr Val
385                 390                 395
```

<210> SEQ ID NO 9
<211> LENGTH: 380
<212> TYPE: PRT
<213> ORGANISM: Arabidopsis sp.

<400> SEQUENCE: 9

Met Thr Phe Arg Ser Leu Leu Gln Glu Met Arg Ser Arg Pro His Arg
 1               5                  10                  15

Val Val His Ala Ala Ser Thr Ala Asn Ser Ser Asp Pro Phe Ser
            20                  25                  30

Trp Ser Glu Leu Pro Glu Glu Leu Leu Arg Glu Ile Leu Ile Arg Val
            35                  40                  45

Glu Thr Val Asp Gly Gly Asp Trp Pro Ser Arg Arg Asn Val Val Ala
 50                  55                  60

Cys Ala Gly Val Cys Arg Ser Trp Arg Ile Leu Thr Lys Glu Ile Val
 65                  70                  75                  80

Ala Val Pro Glu Phe Ser Ser Lys Leu Thr Phe Pro Ile Ser Leu Lys
                85                  90                  95

Gln Ser Gly Pro Arg Asp Ser Leu Val Gln Cys Phe Ile Lys Arg Asn
            100                 105                 110

Arg Asn Thr Gln Ser Tyr His Leu Tyr Leu Gly Leu Thr Thr Ser Leu
        115                 120                 125

Thr Asp Asn Gly Lys Phe Leu Leu Ala Ala Ser Lys Leu Lys Arg Ala
130                 135                 140

Thr Cys Thr Asp Tyr Ile Ile Ser Leu Arg Ser Asp Asp Ile Ser Lys
145                 150                 155                 160

Arg Ser Asn Ala Tyr Leu Gly Arg Met Arg Ser Asn Phe Leu Gly Thr
                165                 170                 175

Lys Phe Thr Val Phe Asp Gly Ser Gln Thr Gly Ala Ala Lys Met Gln
            180                 185                 190

Lys Ser Arg Ser Ser Asn Phe Ile Lys Val Ser Pro Arg Val Pro Gln
        195                 200                 205

Gly Ser Tyr Pro Ile Ala His Ile Ser Tyr Glu Leu Asn Val Leu Gly
    210                 215                 220

Ser Arg Gly Pro Arg Arg Met Arg Cys Ile Met Asp Thr Ile Pro Met
225                 230                 235                 240

Ser Ile Val Glu Ser Arg Gly Val Val Ala Ser Thr Ser Ile Ser Ser
                245                 250                 255

Phe Ser Ser Arg Ser Ser Pro Val Phe Arg Ser His Ser Lys Pro Leu
            260                 265                 270

Arg Ser Asn Ser Ala Ser Cys Ser Asp Ser Gly Asn Asn Leu Gly Asp
        275                 280                 285

Pro Pro Leu Val Leu Ser Asn Lys Ala Pro Arg Trp His Glu Gln Leu
    290                 295                 300

Arg Cys Trp Cys Leu Asn Phe His Gly Arg Val Thr Val Ala Ser Val
305                 310                 315                 320

Lys Asn Phe Gln Leu Val Ala Val Ser Asp Cys Glu Ala Gly Gln Thr
                325                 330                 335

Ser Glu Arg Ile Ile Leu Gln Phe Gly Lys Val Gly Lys Asp Met Phe
            340                 345                 350

Thr Met Asp Tyr Gly Tyr Pro Ile Ser Ala Phe Gln Ala Phe Ala Ile
        355                 360                 365

Cys Leu Ser Ser Phe Glu Thr Arg Ile Ala Cys Glu
    370                 375                 380

```
<210> SEQ ID NO 10
<211> LENGTH: 445
<212> TYPE: PRT
<213> ORGANISM: Arabidopsis sp.

<400> SEQUENCE: 10

Met Ser Phe Arg Gly Ile Val Gln Asp Leu Arg Asp Gly Phe Gly Ser
1               5                   10                  15

Leu Ser Arg Arg Ser Phe Asp Phe Arg Leu Ser Ser Leu His Lys Gly
            20                  25                  30

Lys Ala Gln Gly Ser Ser Phe Arg Glu Tyr Ser Ser Ser Arg Asp Leu
        35                  40                  45

Leu Ser Pro Val Ile Val Gln Thr Ser Arg Trp Ala Asn Leu Pro Pro
    50                  55                  60

Glu Leu Leu Phe Asp Val Ile Lys Arg Leu Glu Glu Ser Glu Ser Asn
65                  70                  75                  80

Trp Pro Ala Arg Lys His Val Val Ala Cys Ala Ser Val Cys Arg Ser
                85                  90                  95

Trp Arg Ala Met Cys Gln Glu Ile Val Leu Gly Pro Glu Ile Cys Gly
            100                 105                 110

Lys Leu Thr Phe Pro Val Ser Leu Lys Gln Pro Gly Pro Arg Asp Ala
        115                 120                 125

Met Ile Gln Cys Phe Ile Lys Arg Asp Lys Ser Lys Leu Thr Phe His
    130                 135                 140

Leu Phe Leu Cys Leu Ser Pro Ala Leu Leu Val Glu Asn Gly Lys Phe
145                 150                 155                 160

Leu Leu Ser Ala Lys Arg Thr Arg Thr Thr Arg Thr Glu Tyr Ile
                165                 170                 175

Ile Ser Met Asp Ala Asp Asn Ile Ser Arg Ser Ser Asn Ser Tyr Leu
            180                 185                 190

Gly Lys Leu Arg Ser Asn Phe Leu Gly Thr Lys Phe Leu Val Tyr Asp
        195                 200                 205

Thr Gln Pro Pro Asn Thr Ser Ser Ser Ala Leu Ile Thr Asp Arg
    210                 215                 220

Thr Ser Arg Ser Arg Phe His Ser Arg Arg Val Ser Pro Lys Val Pro
225                 230                 235                 240

Ser Gly Ser Tyr Asn Ile Ala Gln Ile Thr Tyr Glu Leu Asn Val Leu
                245                 250                 255

Gly Thr Arg Gly Pro Arg Arg Met His Cys Ile Met Asn Ser Ile Pro
            260                 265                 270

Ile Ser Ser Leu Glu Pro Gly Gly Ser Val Pro Asn Gln Pro Glu Lys
        275                 280                 285

Leu Val Pro Ala Pro Tyr Ser Leu Asp Asp Ser Phe Arg Ser Asn Ile
    290                 295                 300

Ser Phe Ser Lys Ser Ser Phe Asp His Arg Ser Leu Asp Phe Ser Ser
305                 310                 315                 320

Ser Arg Phe Ser Glu Met Gly Ile Ser Cys Asp Asp Asn Glu Glu Glu
                325                 330                 335

Ala Ser Phe Arg Pro Leu Ile Leu Lys Asn Lys Gln Pro Arg Trp His
            340                 345                 350

Glu Gln Leu Gln Cys Trp Cys Leu Asn Phe Arg Gly Arg Val Thr Val
        355                 360                 365

Ala Ser Val Lys Asn Phe Gln Leu Val Ala Ala Arg Gln Pro Gln Pro
```

```
                     370                 375                 380
Gln Gly Thr Gly Ala Ala Ala Pro Thr Ser Ala Pro Ala His Pro
385                 390                 395                 400

Glu Gln Asp Lys Val Ile Leu Gln Phe Gly Lys Val Gly Lys Asp Met
                405                 410                 415

Phe Thr Met Asp Tyr Arg Tyr Pro Leu Ser Ala Phe Gln Ala Phe Ala
                420                 425                 430

Ile Cys Leu Ser Ser Phe Asp Thr Lys Leu Ala Cys Glu
                435                 440                 445

<210> SEQ ID NO 11
<211> LENGTH: 380
<212> TYPE: PRT
<213> ORGANISM: Arabidopsis sp.

<400> SEQUENCE: 11

Met Arg Ser Arg Pro His Arg Val Val His Asp Leu Ala Ala Ala
 1               5                  10                  15

Ala Ala Asp Ser Thr Ser Val Ser Ser Gln Asp Tyr Arg Trp Ser Glu
                20                  25                  30

Ile Pro Glu Glu Leu Leu Arg Glu Ile Leu Ile Arg Val Glu Ala Ala
                35                  40                  45

Asp Gly Gly Gly Trp Pro Ser Arg Arg Ser Val Ala Cys Ala Gly
 50                  55                  60

Val Cys Arg Gly Trp Arg Leu Leu Met Asn Glu Thr Val Val Val Pro
 65                  70                  75                  80

Glu Ile Ser Ser Lys Leu Thr Phe Pro Ile Ser Leu Lys Gln Pro Gly
                85                  90                  95

Pro Arg Asp Ser Leu Val Gln Cys Phe Ile Lys Arg Asn Arg Ile Thr
                100                 105                 110

Gln Ser Tyr His Leu Tyr Leu Gly Leu Thr Asn Ser Leu Thr Asp Asp
                115                 120                 125

Gly Lys Phe Leu Leu Ala Ala Cys Lys Leu Lys His Thr Thr Cys Thr
 130                 135                 140

Asp Tyr Ile Ile Ser Leu Arg Ser Asp Asp Met Ser Arg Arg Ser Gln
145                 150                 155                 160

Ala Tyr Val Gly Lys Val Arg Ser Asn Phe Leu Gly Thr Lys Phe Thr
                165                 170                 175

Val Phe Asp Gly Asn Leu Leu Pro Ser Thr Gly Ala Ala Lys Leu Arg
                180                 185                 190

Lys Ser Arg Ser Tyr Asn Pro Ala Lys Val Ser Ala Lys Val Pro Leu
                195                 200                 205

Gly Ser Tyr Pro Val Ala His Ile Thr Tyr Glu Leu Asn Val Leu Gly
 210                 215                 220

Ser Arg Gly Pro Arg Lys Met Gln Cys Leu Met Asp Thr Ile Pro Thr
225                 230                 235                 240

Ser Thr Met Glu Pro Gln Gly Val Ala Ser Glu Pro Ser Glu Phe Pro
                245                 250                 255

Leu Leu Gly Thr Arg Ser Thr Leu Ser Arg Ser Gln Ser Lys Pro Leu
                260                 265                 270

Arg Ser Ser Ser His Leu Lys Glu Thr Pro Leu Val Leu Ser Asn
                275                 280                 285

Lys Thr Pro Arg Trp His Glu Gln Leu Arg Cys Trp Cys Leu Asn Phe
 290                 295                 300
```

```
His Gly Arg Val Thr Val Ala Ser Val Lys Asn Phe Gln Leu Val Ala
305                 310                 315                 320

Ala Gly Ala Ser Cys Gly Ser Gly Thr Gly Met Ser Pro Glu Arg Gln
                325                 330                 335

Ser Glu Arg Ile Ile Leu Gln Phe Gly Lys Val Gly Lys Asp Met Phe
            340                 345                 350

Thr Met Asp Tyr Gly Tyr Pro Ile Ser Ala Phe Gln Ala Phe Ala Ile
        355                 360                 365

Cys Leu Ser Ser Phe Glu Thr Arg Ile Ala Cys Glu
    370                 375                 380

<210> SEQ ID NO 12
<211> LENGTH: 1365
<212> TYPE: DNA
<213> ORGANISM: Arabidopsis sp.

<400> SEQUENCE: 12
atgtcgttcc gtagcatagt tcgtgatgtg agagatagta taggaagtct atcgaggcgt      60
agtttcgact ttaagttaag cagcttgaac aaagaaggtg gtaaatcccg tggttcggtt     120
caagattctc atgaggaaca acttgtagta acgattcaag aaacaccgtg ggcgaatcta     180
cctccagagt tattacgtga tgtgatcaaa gacttgaag agagtgaaag tgtgtggcct      240
gctcgtagac atgttgttgc ttgtgcttct gtttgcaggt catggagaga tatgtgtaaa     300
gagattgttc aaagtccgga gctctcaggc aaaatcacat ttcctgtttc gttgaaacag     360
cctggaccaa gagatgcaac aatgcaatgc tttatcaaaa gggataaatc taacttgact     420
tatcatttat atctttgtct cagtcctgct ttgttggttg agaatggaaa gtttcttctt     480
tctgcaaaac gcataagaag aactacatac accgagtacg tgatctctat gcacgccgac     540
accatttcga gatcaagcaa tacctacatt ggcaaaatca ggtctaattt tctggggacg     600
aagtttataa tatacgatac acaaccagca tacaacagca catcgctcg agcggtccaa      660 ccggtaggtc ttagccgcag attctactca agagagtct ctcccaaagt acctagtggg      720
agctacaaaa ttgcgcaggt ttcttatgag ctaaacgttc ttggtacccg tggtccgagg     780
agaatgcatt gtgcgatgaa ctcaattccc gcctcttccc ttgcggaagg cggaactgtg     840
cctggacagc ccgatatcat tgtcccgcgc tctattctcg acgaatcgtt ccgcagcatt     900
acctcttcgt catcgagaaa aatcacttac gattactcga atgattttag cagtgcacgg     960
tttcccgaca ttcttggccc gttaagcgaa gaccaagaag tggtattaga agaagggaaa    1020
gagcggaatt cgccaccact tgtgcttaag aacaagccgc cgaggtggca tgaacagctt    1080
cagtgttggt gtttaaactt caggggacgt gtaacagtcg catcagttaa gaactttcag    1140
ctcattgcag caaaccaacc acagcctcag cctcagcctc aaccgcaacc tcaaccccta    1200
actcagccgc aaccgtctgg tcagaccgat ggtcccgaca agatcatatt gcagtttggg    1260
aaagtgggaa agacatgtt cacgatggat ttccggtatc cgctctctgc gtttcaggct    1320
ttcgctatct gtttgagcag tttcgacaca aaacttgctt gcgaa               1365

<210> SEQ ID NO 13
<211> LENGTH: 1182
<212> TYPE: DNA
<213> ORGANISM: Arabidopsis sp.

<400> SEQUENCE: 13
atgtctttga aaagcatcct tcgtgatctg aaggaagtga gggatggact tggaggcatc      60
```

-continued

| | |
|---|---|
| tccaagagaa gctggtcaaa gtcgtctcac attgctcctg atcaaacaac tccaccactg | 120 |
| gataacatac cacagagccc atgggcttct ttgccgcctg agttgcttca tgacattatc | 180 |
| tggagggttg aagagagtga gacagcttgg cccgctcgag ctgccgttgt ctcttgtgct | 240 |
| tcagtatgta aatcatggag aggaatcact atggagattg tgaggatccc tgagcagtgt | 300 |
| gggaagctca cttttccaat ctcattgaaa cagccgggc ctcgagactc tccaattcaa | 360 |
| tgttttatta agaggaacag agcaacagct acatacattc tctattatgg tttgatgcct | 420 |
| tcggagactg agaacgacaa actgttgtta gcagcaagaa ggattagaag agcgacatgc | 480 |
| acagacttta taatctccct atctgcaaag aacttctcac ggagcagcag tacttatgtt | 540 |
| ggcaaattaa ggtctggttt tctgggaacc aagttcacaa tatatgacaa ccaaacagca | 600 |
| tcatccacag cacaagccca acctaaccga agactccacc cgaaacaagc ggctcctaaa | 660 |
| ctacctacga atagctctac cgtaggaaac ataacctacg agctcaatgt tcttcgcaca | 720 |
| aggggaccta gaagaatgca ctgcgctatg gattctatac ccctctcttc tgttattgct | 780 |
| gaaccgtcag tagttcaagg catagaagag gaagtctctt cctctccttc accaaaagga | 840 |
| gaaaccatca aacagacaa agagattcct gataattctc caagcttaag ggaccaaccg | 900 |
| ctagttctca aaaacaaatc cccaagatgg catgagcagt tgcagtgctg gtgcctcaac | 960 |
| ttcaagggaa gagtgactgt ggcttcagtt aagaatttcc agcttgttgc agagattgac | 1020 |
| gcttctttgg atgcgccgcc tgaagaacat gagagggtga tcttacagtt tggcaaaatc | 1080 |
| ggtaaggata ttttcaccat ggattatcgc taccctctat ctgcttttca agcctttgct | 1140 |
| atatgcatta gcagctttga caccaaaccg gcatgtgaag gg | 1182 |

<210> SEQ ID NO 14
<211> LENGTH: 1218
<212> TYPE: DNA
<213> ORGANISM: Arabidopsis sp.

<400> SEQUENCE: 14

| | |
|---|---|
| atgtccttca agagtctcat tcaggacatg agaggagagc ttgggagtat atccagaaag | 60 |
| ggattcgatg tcagattcgg gtatggtaga tccaggtctc aacgtgttgt tcaggatact | 120 |
| tctgttcctg ttgatgcttt caagcagagc tgctgggcta gtatgcctcc ggagctcctg | 180 |
| agagatgttc ttatgaggat tgagcaatcc gaagacactt ggccgtctag gaaaaatgtt | 240 |
| gtttcttgcg ctggtgtctg caggaactgg cgagaaatcg tcaaagagat cgtcagagtt | 300 |
| cctgagcttt ctagcaaact cacttttcct atctccctca aacagccggg tcctagagga | 360 |
| tcacttgttc aatgctatat tatgagaaac cgcagcaatc aaacctacta tctataccctc | 420 |
| gggttaaacc aagcagcttc aaatgatgat ggaaagttcc ttcttgctgc caagaggttt | 480 |
| cggaggccaa cttgcactga ctacatcatc tccttaaact gcgatgatgt ctctcgagga | 540 |
| agcaatacct atatcggaaa gcttagatct aactttctgg ggaccaagtt cactgtctat | 600 |
| gacgctcagc cgacgaatcc tggaactcag gttaccagaa cccgttcaag cagacttctc | 660 |
| agtttgaaac aagtgagccc gagaattcca tctggcaact atcctgtagc acatatctca | 720 |
| tatgagctta acgtcttggg ttccagagga ccgaggagga tgcagtgtgt catggatgcc | 780 |
| atccctgcat cagctgtaga acctggagga acagctccaa ctcagacgga acttgtccat | 840 |
| agcaatcttg atagtttccc ctcattctcc ttcttcaggt cgaaatcaat tcgtgcagag | 900 |
| agtctccctt ctggtccatc atctgctgct cagaaggaag gactgcttgt cctgaaaaac | 960 |
| aaagcgccca gatggcacga acagctccag tgctggtgcc tcaacttcaa tgggagagtc | 1020 |

-continued

```
acagttgctt ccgtcaaaaa ctttcagctg gtagctgctc ctgagaatgg acctgcagga      1080
cctgagcacg aaaacgtgat tctccagttt ggaaaagtcg aaaagatgt gttcacaatg       1140 gattatcagt accctatctc tgccttccag gccttcacca tttgcctcag cagtttcgac      1200
accaagatag catgtgaa                                                    1218

<210> SEQ ID NO 15
<211> LENGTH: 795
<212> TYPE: DNA
<213> ORGANISM: Arabidopsis sp.

<400> SEQUENCE: 15
atgcctcctg agcttctgag agatgttctg atgaggatag agcgatccga agacacttgg       60
ccttctagga agaatgttgt tcttgtgta ggtgtgtgta agaactggcg acaaatattc       120
aaagagatcg ttaacgttcc tgaggtttct agcaaattca cttttccaat ctccttgaaa      180
cagcctggtc caggaggatc acttgttcaa tgctatgtta agagaaaccg tagcaatcaa      240
actttctatc tataccttgg aggtgaagca aaaatatttt gtcagtctga accaagtgat      300
atttatctcg ttccttacag ttacagagag acgcattgcg tcatggatgc catctctgca      360
tcagcagtaa aacctggagg aacagctaca actcagacag aactcgataa tttcgtgtca      420
ttcaggtctc cttctggtca aaaggaagga gtgcttgttc ttaagagcaa agtgcctaga      480
ttggaagaac agagctggtg tctcgacttc aatggctctc ctgagaacga acctgagaat      540
gaaaacgaca ttttccagtt tgcgaaagtc ggaaacttgc acaaactctt cagtttatat      600
gaggctgaat ggattcctct cgttcgcacc tcagtgtttg ctgtcattgc tcgagtttgt      660
agagataaaa agcatacacc atcgtatgaa ttgaaacttg cattgtactt tgcaaaaaac      720
tctgcaatcc tcaagaaatt cgttctccgc ggttacactc gagaagaaga tttactcgca      780
ttgcccgtgg ctaac                                                      795

<210> SEQ ID NO 16
<211> LENGTH: 1287
<212> TYPE: DNA
<213> ORGANISM: Arabidopsis sp.

<400> SEQUENCE: 16
atgtcgtttc tgagtattgt tcgtgatgtt agagatactg taggaagctt ttcgagacgt       60
agtttcgacg tgagagtatc taatgggacg actcatcaga ggagtaaatc tcacggtgtt      120
gaggcacata ttgaagatct tattgtaatc aagaacactc gttgggctaa tttaccggct      180
gcgctattac gagatgtgat gaaaagttg gatgaaagcg agagtacttg gcctgcacgt      240
aaacaagtcg ttgcttgtgc tggtgtctgc aagacatgga gactaatgtg caaagatatt      300
gtgaaaagtc ctgagttctc aggcaaactc acatttccag tttcgttgaa acagcccggg      360
cctagggatg gaatcataca atgttatatc aaaagagaca agtctaacat gacttaccac      420
ctttaccttt ctcttagtcc tgccatactt gttgaaagtg ggaagtttct tctctcggca      480
aagcgctcac ggagagctac atacacagag tatgtaatat caatggatgc agacaacatt      540
tcaagatcaa gcagcactta cattggcaaa ctgaagtcta actttctagg gacaaaattt      600
atagtatatg atacggctcc tgcgtacaac agtagccaga tattgtcccc accaaaccgg      660
agtcgtagtt tcaactccaa gaaagtgtct cccaaagtcc cttctggaag ttacaacatt      720
gctcaagtta catacgagct gaacttgctt ggaacccgtg gacctcgtag aatgaactgc      780
```

```
attatgcact ctatcccctc cttagctcta gaacccggag gtactgtccc tagccaacct      840
gagtttctac aacgttccct tgatgaatct ttccgcagca tcggttcctc aaagatagtc      900
aaccactcgg gagatttcac ccgaccgaaa gaggaagaag gaaaggtgcg acctttggta      960
ctgaaaacta aaccgccaag gtggctccaa ccgttgcgat gttggtgcct taacttcaaa     1020
gggagagtga ctgtagcttc tgtcaagaac ttccagttga tgtccgctgc aacggttcag     1080
cccggtagtg gtagtgatgg tggagcattg gctacgaggc catcgttatc accacagcag     1140
ccagagcaat caaaccatga taagataata ctacactttg ggaaagtggg taaggatatg     1200
ttcactatgg actatcgtta tcctctctct gcctttcaag cgtttgccat ttccctgagc     1260
acctttgata ctaaattggc atgtgaa                                         1287

<210> SEQ ID NO 17
<211> LENGTH: 1164
<212> TYPE: DNA
<213> ORGANISM: Arabidopsis sp.

<400> SEQUENCE: 17
atgtcattga agaacatagt gaagaacaaa tacaaagcta ttggtagaag agggaggtca       60
cacattgcac cagaaggatc atctgtgtct tcttctttat caactaatga aggtttaaac      120
cagagtattt gggttgattt gcctccagag ttacttcttg atataatcca aaggattgag      180
tctgaacaga gtttatggcc ggggaggaga gatgttgttg cttgtgcttc ggtttgtaag      240
tcatggaggg agatgactaa agaagttgtt aaagttcctg agctctctgg tttgatcacg      300
tttccgattt cttttaagaca gcctggacct agagatgctc caattcaatg ctttattaaa      360
cgtgaaagag ctacggggat ataccgtctc tatcttggtt taagccctgc tctttccggt      420
gacaagagta agttgttgtt atctgcaaag agagtcagga gagcgacggg tgcggagttt      480
gttgtatcgt tatcggggaa tgacttctcg agaagtagta gtaattacat aggaaaaactg      540 agatcaaatt tcctgggaac gaagttcaca gtctacgaaa accaacctcc tccgtttaac      600
cgaaagctcc caccatcgat gcaagtgtct ccatgggtat cgtcgtcatc tagtagttac      660
aacatagctt caatcttgta tgagctgaat gttctgagaa ccagaggtcc aagaagaatg      720
caatgtataa tgcacagtat cccgatttca gcgattcaag aaggcggcaa aatccagtcg      780
ccaacggagt tcacaaacca aggaaagaag aagaagaagc cgctgatgga tttctgctca      840
gggaacctgg gagagaatc cgttataaaa gaaccattaa ttctgaaaaa caagtcgccg      900
agatggcacg aacagcttca gtgctggtgt ctaaacttca aaggtcgagt cacagtcgcc      960
tcggtgaaaa acttccagct agtggcagct gctgcagaag cagggaagaa catgaacata     1020
ccagaagagg aacaagatag agtgatatta cagtttggga agataggcaa agacattttc     1080
acaatggatt atcgttaccc gatctctgca ttccaagctt ttgctatttg tttaagcagc     1140
ttcgacacga agccagtctg cgaa                                            1164

<210> SEQ ID NO 18
<211> LENGTH: 1137
<212> TYPE: DNA
<213> ORGANISM: Arabidopsis sp.

<400> SEQUENCE: 18
atgcctttgt cacggtccct cctttcgcgg aggatctcga actcttttag gtttcatcag       60
ggagagacaa cgacggcacc ggaatccgaa tcgattcctc cgccgtcgaa tatggccggt      120
tcttcgtcat ggtcggcgat gctccctgaa ttattaggcg agatcattcg tcgcgtggag      180
```

```
gagactgagg accgttggcc tcaacgtcgt gatgtagtta cttgcgcttg cgtttctaag    240
aaatggagag aaatcactca cgatttcgct agatcctctc ttaactctgg caaaattact    300
ttcccttctt gcctcaaatt gccaggtcct agagactttt ctaatcagtg cttgataaag    360
aggaacaaga agacatcaac gttttacttg tatcttgctc taacaccatc attcactgat    420
aagggaaagt ttcttctggc ggcgcggagg tttaggaccg gtgcttacac tgagtacatc    480
atatcacttg atgctgatga tttctctcaa ggaagtaatg cctacgtcgg aaaattaaga    540
tcagattttc ttgggaccaa ctttacagta tacgatagcc aaccaccaca caacggagca    600
aaaccttcaa atggcaaagc cagtcgcaga tttgcatcaa agcagataag ccctcaagtt    660
ccagcaggca actttgaagt cggtcatgtt tcttataaat tcaaccttt gaaatcaaga    720 ggtccaagaa gaatggtaag cacactccga tgcccatcac catcaccttc atcatcatcc    780
gctggactct cgtctgacca aaagccatgt gatgtaacca agataatgaa aaaacccaac    840
aaggatggtt ccagcttgac aatactaaag aacaaagctc ctagatggca cgagcacttg    900
cagtgctggt gtctgaactt ccatggacga gttactgttg cttcggtcaa gaactttcag    960
ctggttgcga ccgttgacca aagtcaaccg agcggtaaag gcgatgaaga aacagttctt   1020
ctacagtttg gtaaagtggg agatgacact ttcactatgg attatagaca gcctctctct   1080
gcatttcagg cttttgctat ctgtctcaca gtttcggca ctaaacttgc ctgcgag       1137

<210> SEQ ID NO 19
<211> LENGTH: 1191
<212> TYPE: DNA
<213> ORGANISM: Arabidopsis sp.

<400> SEQUENCE: 19
atggctggtt cgagaaaagt gaatgatttg ttggaggaaa ataagggaaa tgtggacaca     60
attacagggt ctttatccac tcaaaaggga gaggataagg agaatgtgtc gccggagaaa    120
gtctctacct ctgtggaaac tcggaaacta gatcgagctt tgaagtctca atcgatgaag    180
ggtaactctg gtttccaac ggaagttaca aatttcaaat cttctctcaac tggtggtcga    240 acagctctga agcagtcatc actgcaagcg tgtatgcaga agaacagtga ggttgataag    300
agtagtttcg gaatgaaaac ttggactagt gttgattcag agcattcaag ttcgttgaaa    360
gtgtgggagt tttcggattc tgaagctgcc cctgcttcct cttggtctac tttgcccaac    420 agggcttttgt tgtgcaagac actaccttgt gatgtgggaa gatgcacttg tctgattgtg    480
aaagaacaat cacctgaagg cttgagccac ggatctgtat attcactttta tacacatgaa    540 ggtcgggggc gtaaagaccg gaagttagca gttgcttacc atagccgacg taatgggaaa    600
tctatattta gggtggcaca gaatgttaag ggattgctgt gcagttcgga tgaaagttat    660
gtcggttcca tgacggctaa tctcttgggt tccaagtact acatatggga caagggagtt    720
cgagttggtt ctgtaggtaa aatggtgaag ccgcttcttt cggttgtaat attcacaccc    780
accataacaa cttggacagg gagctacaga agaatgagaa cttttgctacc aaagcagcag    840 ccaatgcaga aaacaacaa taagcaggtt caacaagcta gtaaactacc gcttgattgg    900
cttgagaata aggaaaaaat tcagaagcta tgctcaagga taccacatta caacaaaatc    960
tccaagcagc atgagttaga cttcagagac agaggaagaa caggactgag aatacagagc   1020
tcggtgaaga actttcagct aacactcacg gagactccaa ggcagacaat tcttcaaatg   1080
gggagagttg acaaagcaag atatgtaatc gacttcaggt atccattctc aggctaccaa   1140
```

| gcattctgca tttgcttggc ttctattgat tccaagcttt gttgtactgt t | 1191 |

<210> SEQ ID NO 20
<211> LENGTH: 1140
<212> TYPE: DNA
<213> ORGANISM: Arabidopsis sp.

<400> SEQUENCE: 20

| atgacgttcc gaagtttact ccaggaaatg cggtctaggc cacaccgtgt agttcacgcc | 60 |
| gccgcctcaa ccgctaatag ttcagaccct ttcagctggt cggagctccc ggaggagctg | 120 |
| cttagagaaa tcctgattag ggttgagact gttgacggcg gcgattggcc gtcgcggcga | 180 |
| aacgtggtgg cttgtgccgg cgtttgtcgt agctggagga ttctcaccaa ggagattgta | 240 |
| gctgttcctg aattctcctc taaattgact ttccctatct ccctcaagca gtctggtcca | 300 |
| agagattctc tagttcaatg ctttataaaa cgtaatcgaa atactcaatc gtatcatctc | 360 |
| tatctcggat taactacctc tttgacggat aacgggaagt tcttcttgc tgcttctaag | 420 |
| ctgaagcgcg caacttgcac tgattacatc atctctttgc gttcagacga tatctcaaag | 480 |
| agaagcaacg cgtatcttgg gagaatgaga tcgaacttcc ttggaacaaa attcacggtc | 540 |
| tttgatggta gtcagaccgg agcagcgaag atgcagaaga gccgctcttc taatttcatc | 600 |
| aaagtttcac ctagagttcc tcagggaagt taccccatcg ctcacatttc atacgagtta | 660 |
| aacgtcttag gctctcgggg accgagaaga atgcgttgca tcatggatac aatacctatg | 720 |
| agcatcgtgg agtcgcgagg agtagtagct tcaacatcca taagctcttt ttccagtcgg | 780 |
| tcatcaccag tctttaggtc tcactcaaaa ccattgcgca gtaatagtgc atcatgtagc | 840 |
| gactcaggca acaacctggg agatccacca ttggtgctga gcaacaaagc tccacggtgg | 900 |
| catgagcagt tacgttgctg gtgcttaaat ttccatggtc gagtcacagt ggcttcggtt | 960 |
| aagaactttc agcttgtggc agttagtgac tgtgaagcag ggcagacatc tgagaggatc | 1020 |
| atactccagt ttgggaaagt tgggaaggac atgtttacca tggattatgg atatccgatt | 1080 |
| tctgcgtttc aagcgtttgc tatctgcctg agcagttttg aaaccagaat tgcctgtgaa | 1140 |

<210> SEQ ID NO 21
<211> LENGTH: 1335
<212> TYPE: DNA
<213> ORGANISM: Arabidopsis sp.

<400> SEQUENCE: 21

| atgtcgtttc gaggcattgt tcaagatttg agagatgggt ttgggagctt gtcaaggagg | 60 |
| agtttcgatt ttaggctctc gagtcttcat aaagggaaag ctcagggttc ttcgttccgt | 120 |
| gagtattcgt catcccgtga tctcttgtcg cctgtgatag ttcagacaag tagatgggct | 180 |
| aatcttcctc cagagttact ctttgatgtg atcaaaagat tagaggaaag tgagagtaat | 240 |
| tggcctgcaa gaaaacatgt tgtggcttgt gcttcggttt gtcggtcttg gagagctatg | 300 |
| tgccaagaga ttgttttggg gcctgaaatc tgtgggaaac tcactttccc tgtttccctc | 360 |
| aaacagccag ggcctcgtga tgcaatgatt cagtgtttca tcaaaaggga taatcaaag | 420 |
| ctaacatttc acctttttct ttgtttaagt cccgctctat tagtggagaa tgggaaattt | 480 |
| cttctttcag ctaaaagaac tcgtagaact actcgaaccg agtacattat ctccatggat | 540 |
| gctgataaca tctcaagatc cagcaactct tacctcggaa agctcagatc aaacttcctt | 600 |
| gggacaaagt tcttggtgta cgacacgcaa ccaccaccaa acacatcttc gagcgcactt | 660 |
| atcactgatc gaacaagccg aagcaggttt cactccagac gagtttctcc taaagtacca | 720 |

```
tccggaagct acaacattgc tcaaatcacc tatgagctca acgtgttggg cacacgcggg      780
ccacgacgaa tgcactgcat catgaactcc atcccaattt catcgctcga accaggcggt      840
tcagtcccta accaacccga gaaactcgtc cctgcaccat actctctcga cgactcattc      900
cgcagtaaca tctccttctc caaatcatca tttgaccacc gctccctcga tttcagcagt      960
tctagattct ccgaaatggg aatatcctgc gacgacaacg aagaagaagc gagtttcaga     1020
ccgttgattc taaagaacaa gcagccaagg tggcacgagc agttgcaatg ctggtgtttg     1080
aatttccgcg gacgtgtgac agttgcatcg gttaagaatt ccagcttgt  agcagcaaga    1140 cagccgcagc ctcaagggac aggtgcagca gcagcaccaa caagtgcacc tgctcaccct     1200
gagcaagaca aggtgattct ccagtttggt aaagtaggga aagatatgtt cacaatggac     1260
tataggtatc cattatcggc gtttcaggcg tttgcgatat gcttaagcag ctttgacacc     1320
aagcttgctt gtgaa                                                     1335

<210> SEQ ID NO 22
<211> LENGTH: 1140
<212> TYPE: DNA
<213> ORGANISM: Arabidopsis sp.

<400> SEQUENCE: 22
atgcgttcga gaccgcatcg tgtggtccac gaccttgccg ccgccgcagc tgccgattcc       60
acttctgtgt catcgcaaga ttatcgctgg tcagagattc ctgaagagct tcttagggag      120
attctgattc gtgttgaagc ggcggacggt ggcggatggc cgtcacgacg cagcgtggtg      180
gcttgtgccg gcgtttgtcg tggctggcgg ctacttatga acgaaaccgt cgttgtccct      240
gagatctctt ctaagttgac tttccccatc tctctcaagc agcctggtcc aagggattca      300
ctggttcaat gctttatcaa acgtaatcga attacgcaat catatcatct ctatctcgga      360
ttaaccaact ctttaacgga tgatgggaag tttttgcttg ctgcgtgtaa gttgaagcac      420
acaacttgta cggattacat tatctcttta cgttctgatg atatgtcgag aagaagccaa      480
gcttatgttg gcaaagtgag atcgaacttc ctaggaacga aattcactgt ctttgatgga      540
aatctgctgc cttcaacggg agccgcaaag ttgagaaaga gccgatctta taatcccgca      600
aaagtttcag caaagttcc tcttggaagt tatcctgtcg ctcatatcac atatgagctg      660
aatgtcttag gatcccgggg accaagaaag atgcaatgtc ttatggacac aatacctaca      720
agcacaatgg agcctcaagg agtagcttca gaaccatcag agtttccctt actcggtact      780
cggtcaacct tatccaggtc tcagtcaaaa ccattacgca gtagctcaag ccacctgaaa      840
gaaacaccat tagtgctgag caacaagaca ccacggtggc acgagcagct acgctgctgg      900
tgcttgaatt ccatggccg  tgtcacagta gcgtcagtga agaactttca gctcgtggca      960
gcaggagcta gctgtggcag tggcacggga atgtcaccgg agaggcagag cgagcggatt     1020
atattgcagt ttgggaaagt cgggaaagat atgttcacga tggattatgg atacccgatc     1080
tcagctttcc aggcttttgc catttgcttg agcagctttg agactagaat cgcttgtgaa     1140

<210> SEQ ID NO 23
<211> LENGTH: 24
<212> TYPE: DNA
<213> ORGANISM: Artificial Sequence
<220> FEATURE:
<223> OTHER INFORMATION: Primer

<400> SEQUENCE: 23
```
atgtcgttcc gtagcatagt tcgt                                              24

<210> SEQ ID NO 24
<211> LENGTH: 25
<212> TYPE: DNA
<213> ORGANISM: Artificial Sequence
<220> FEATURE:
<223> OTHER INFORMATION: Primer

<400> SEQUENCE: 24
ttattcgcaa gcaagttttg tgtcg                                             25

<210> SEQ ID NO 25
<211> LENGTH: 28
<212> TYPE: DNA
<213> ORGANISM: Artificial Sequence
<220> FEATURE:
<223> OTHER INFORMATION: Primer

<400> SEQUENCE: 25
atgtctttga aaagcatcct tcgtgatc                                          28

<210> SEQ ID NO 26
<211> LENGTH: 28
<212> TYPE: DNA
<213> ORGANISM: Artificial Sequence
<220> FEATURE:
<223> OTHER INFORMATION: Primer

<400> SEQUENCE: 26
ttacccttca catgccggtt tggtgtca                                          28

<210> SEQ ID NO 27
<211> LENGTH: 24
<212> TYPE: DNA
<213> ORGANISM: Artificial Sequence
<220> FEATURE:
<223> OTHER INFORMATION: Primer

<400> SEQUENCE: 27
atgtccttca agagtctcat tcag                                              24

<210> SEQ ID NO 28
<211> LENGTH: 24
<212> TYPE: DNA
<213> ORGANISM: Artificial Sequence
<220> FEATURE:
<223> OTHER INFORMATION: Primer

<400> SEQUENCE: 28
tcattcacat gctatcttgg tgtc                                              24

<210> SEQ ID NO 29
<211> LENGTH: 23
<212> TYPE: DNA
<213> ORGANISM: Artificial Sequence
<220> FEATURE:
<223> OTHER INFORMATION: Primer

<400> SEQUENCE: 29
atgtcgtttc tgagtattgt tcg                                               23

<210> SEQ ID NO 30
<211> LENGTH: 23
<212> TYPE: DNA
<213> ORGANISM: Artificial Sequence -continued

```
<220> FEATURE:
<223> OTHER INFORMATION: Primer

<400> SEQUENCE: 30
ttattcacat gccaatttag tat                                              23

<210> SEQ ID NO 31
<211> LENGTH: 23
<212> TYPE: DNA
<213> ORGANISM: Artificial Sequence
<220> FEATURE:
<223> OTHER INFORMATION: Primer

<400> SEQUENCE: 31
atgtcattga agaacatagt gaa                                              23

<210> SEQ ID NO 32
<211> LENGTH: 23
<212> TYPE: DNA
<213> ORGANISM: Artificial Sequence
<220> FEATURE:
<223> OTHER INFORMATION: Primer

<400> SEQUENCE: 32
tcattcgcag actggcttcg tgt                                              23

<210> SEQ ID NO 33
<211> LENGTH: 21
<212> TYPE: DNA
<213> ORGANISM: Artificial Sequence
<220> FEATURE:
<223> OTHER INFORMATION: Primer

<400> SEQUENCE: 33
atgcctttgt cacggtccct c                                                21

<210> SEQ ID NO 34
<211> LENGTH: 22
<212> TYPE: DNA
<213> ORGANISM: Artificial Sequence
<220> FEATURE:
<223> OTHER INFORMATION: Primer

<400> SEQUENCE: 34
tcactcgcag gcaagtttag tg                                               22

<210> SEQ ID NO 35
<211> LENGTH: 23
<212> TYPE: DNA
<213> ORGANISM: Artificial Sequence
<220> FEATURE:
<223> OTHER INFORMATION: Primer

<400> SEQUENCE: 35
atggctggtt cgagaaaagt gaa                                              23

<210> SEQ ID NO 36
<211> LENGTH: 23
<212> TYPE: DNA
<213> ORGANISM: Artificial Sequence
<220> FEATURE:
<223> OTHER INFORMATION: Primer

<400> SEQUENCE: 36
tcaaacagta caacaaagct tgg                                              23
```

```
<210> SEQ ID NO 37
<211> LENGTH: 23
<212> TYPE: DNA
<213> ORGANISM: Artificial Sequence
<220> FEATURE:
<223> OTHER INFORMATION: Primer

<400> SEQUENCE: 37
atgacgttcc gaagtttact cca                                      23

<210> SEQ ID NO 38
<211> LENGTH: 23
<212> TYPE: DNA
<213> ORGANISM: Artificial Sequence
<220> FEATURE:
<223> OTHER INFORMATION: Primer

<400> SEQUENCE: 38
ttattcacag gcaattctgg ttt                                      23

<210> SEQ ID NO 39
<211> LENGTH: 23
<212> TYPE: DNA
<213> ORGANISM: Artificial Sequence
<220> FEATURE:
<223> OTHER INFORMATION: Primer

<400> SEQUENCE: 39
atgtcgtttc gaggcattgt tca                                      23

<210> SEQ ID NO 40
<211> LENGTH: 23
<212> TYPE: DNA
<213> ORGANISM: Artificial Sequence
<220> FEATURE:
<223> OTHER INFORMATION: Primer

<400> SEQUENCE: 40
ctattcacaa gcaagcttgg tgt                                      23

<210> SEQ ID NO 41
<211> LENGTH: 23
<212> TYPE: DNA
<213> ORGANISM: Artificial Sequence
<220> FEATURE:
<223> OTHER INFORMATION: Primer

<400> SEQUENCE: 41
atgtcgtttc tgagtattgt tcg                                      23

<210> SEQ ID NO 42
<211> LENGTH: 23
<212> TYPE: DNA
<213> ORGANISM: Artificial Sequence
<220> FEATURE:
<223> OTHER INFORMATION: Primer

<400> SEQUENCE: 42
ttattcacat gccaatttag tat                                      23

<210> SEQ ID NO 43
<211> LENGTH: 23
<212> TYPE: DNA
<213> ORGANISM: Artificial Sequence
<220> FEATURE:
<223> OTHER INFORMATION: Primer
```

```
<400> SEQUENCE: 43
atttctcaaa atcttaaaaa ctt                                                    23

<210> SEQ ID NO 44
<211> LENGTH: 20
<212> TYPE: DNA
<213> ORGANISM: Artificial Sequence
<220> FEATURE:
<223> OTHER INFORMATION: Primer

<400> SEQUENCE: 44
tgatagtttt cccagtcaac                                                        20

<210> SEQ ID NO 45
<211> LENGTH: 21
<212> TYPE: DNA
<213> ORGANISM: Artificial Sequence
<220> FEATURE:
<223> OTHER INFORMATION: Primer

<400> SEQUENCE: 45
atgacgttcc gaagtttact c                                                      21

<210> SEQ ID NO 46
<211> LENGTH: 21
<212> TYPE: DNA
<213> ORGANISM: Artificial Sequence
<220> FEATURE:
<223> OTHER INFORMATION: Primer

<400> SEQUENCE: 46
tggttcacgt agtgggccat c                                                      21

<210> SEQ ID NO 47
<211> LENGTH: 21
<212> TYPE: DNA
<213> ORGANISM: Artificial Sequence
<220> FEATURE:
<223> OTHER INFORMATION: Primer

<400> SEQUENCE: 47
ttattcacag gcaattctgg t                                                      21

<210> SEQ ID NO 48
<211> LENGTH: 21
<212> TYPE: DNA
<213> ORGANISM: Artificial Sequence
<220> FEATURE:
<223> OTHER INFORMATION: Primer

<400> SEQUENCE: 48
tggttcacgt agtgggccat c                                                      21
```

PLANT TUBBY-LIKE PROTEINS

RELATED APPLICATION

This application claims priority to U.S. Provisional Application Ser. No. 60/441,380, filed on Jan. 21, 2003, the contents of which are incorporated by reference in their entirety.

BACKGROUND

Various environmental factors, e.g., high salinity, pathogens, and chilling, cause stress and adverse effects on growth and productivity of crops. It is therefore desirable to produce transgenic crops that are tolerant to such factors. Genetic engineering can be used to modify proteins that are involved in regulating responses of plants to environmental factors, thereby improving stress-tolerance.

TUBBY proteins, a group of membrane-bound transcription regulators, were first identified from obese mice via positional cloning (Kleyn et al., 1996, Cell 85: 281-290 and Noben-Trauth et al., 1996, Nature 380: 534-538.). Mutations in the TUBBY genes lead to maturity-onset obesity, insulin resistance, retinal degeneration, and neurosensory hearing loss. TUBBY-like proteins (TLPs) were subsequently discovered in other mammals and were found to be activated through G-proteins, which, in higher plants, are involved in the response to environmental factors and hormone regulation (Warpeha et al., 1991, Proc. Natl. Acad. Sci. 88: 8925-8929, and Ueguchi-Tanaka et al., Proc. Natl. Acad. Sci. 97: 11638-11643).

SUMMARY

This invention is based on the discovery of eleven *Arabidopsis* TUBBY-like proteins, designated as AtTLPs 1-11. These proteins regulate the response of *Arabidopsis* to environmental factors. The full-length AtTLPs 1-11 polypeptides (designated as SEQ ID NOs: 1-11), and cDNAs encoding the polypeptides (designated as SEQ ID NOs: 12-22), are shown below:

```
AtTLP1:
polypeptide:
     1      MSFRSIVRDV RDSIGSLSRR SFDFKLSSLN KEGGKSRGSV QDSHEEQLVV  (SEQ ID NO: 1)

51      TIQETPWANL PPELLRDVIK RLEESESVWP ARRHVVACAS VCRSWRDMCK

101      EIVQSPELSG KITFPVSLKQ PGPRDATMQC FIKRDKSNLT YHLYLCLSPA

151      LLVENGKFLL SAKRIRRTTY TEYVISMHAD TISRSSNTYI GKIRSNFLGT

201      KFIIYDTQPA YNSNIARAVQ PVGLSRRFYS KRVSPKVPSG SYKIAQVSYE

251      LNVLGTRGPR RMHCAMNSIP ASSLAEGGTV PGQPDIIVPR SILDESFRSI

301      TSSSSRKITY DYSNDFSSAR FSDILGPLSE DQEVVLEEGK ERNSPPLVLK

351      NKPPRWHEQL QCWCLNFRGR VTVASVKNFQ LIAANQPQPQ PQPQPQPQPL

401      TQPQPSGQTD GPDKIILQFG KVGKDMFTMD FRYPLSAFQA FAICLSSFDT

451      KLACE cDNA:
     1      ATGTCGTTCC GTAGCATAGT TCGTGATGTG AGAGATAGTA TAGGAAGTCT  (SEQ ID NO: 12)

51      ATCGAGGCGT AGTTTCGACT TTAAGTTAAG CAGCTTGAAC AAAGAAGGTG

101      GTAAATCCCG TGGTTCGGTT CAAGATTCTC ATGAGGAACA ACTTGTAGTA

151      ACGATTCAAG AAACACCGTG GGCGAATCTA CCTCCAGAGT TATTACGTGA

201      TGTGATCAAA AGACTTGAAG AGAGTGAAAG TGTGTGGCCT GCTCGTAGAC

251      ATGTTGTTGC TTGTGCTTCT GTTTGCAGGT CATGGAGAGA TATGTGTAAA

301      GAGATTGTTC AAAGTCCGGA GCTCTCAGGC AAAATCACAT TTCCTGTTTC

351      GTTGAAACAG CCTGGACCAA GAGATGCAAC AATGCAATGC TTTATCAAAA

401      GGGATAAATC TAACTTGACT TATCATTTAT ATCTTTGTCT CAGTCCTGCT

451      TTGTTGGTTG AGAATGGAAA GTTTCTTCTT TCTGCAAAAC GCATAAGAAG

501      AACTACATAC ACCGAGTACG TGATCTCTAT GCACGCCGAC ACCATTTCGA

551      GATCAAGCAA TACCTACATT GGCAAAATCA GGTCTAATTT TCTGGGGACG

601      AAGTTTATAA TATACGATAC ACAACCAGCA TACAACAGCA ACATCGCTCG

651      AGCGGTCCAA CCGGTAGGTC TTAGCCGCAG ATTCTACTCA AAGAGAGTCT

701      CTCCCAAAGT ACCTAGTGGG AGCTACAAAA TTGCGCAGGT TTCTTATGAG
```

```
                             -continued
 751         CTAAACGTTC TTGGTACCCG TGGTCCGAGG AGAATGCATT GTGCGATGAA

801         CTCAATTCCC GCCTCTTCCC TTGCGGAAGG CGGAACTGTG CCTGGACAGC

851         CCGATATCAT TGTCCCGCGC TCTATTCTCG ACGAATCGTT CCGCAGCATT

901         ACCTCTTCGT CATCGAGAAA AATCACTTAC GATTACTCGA ATGATTTTAG

951         CAGTGCACGC TTTTCCGACA TTCTTGGCCC GTTAAGCGAA GACCAAGAAG

1001         TGGTATTAGA AGAAGGGAAA GAGCGGAATT CGCCACCACT TGTGCTTAAG

1051         AACAAGCCGC CGAGGTGGCA TGAACAGCTT CAGTGTTGGT GTTTAAACTT

1101         CAGGGGACGT GTAACAGTCG CATCAGTTAA GAACTTTCAG CTCATTGCAG

1151         CAAACCAACC ACAGCCTCAG CCTCAGCCTC AACCGCAACC TCAACCCCTA

1201         ACTCAGCCGC AACCGTCTGG TCAGACCGAT GGTCCCGACA AGATCATATT

1251         GCAGTTTGGG AAAGTGGGAA AAGACATGTT CACGATGGAT TTCCGGTATC

1301         CGCTCTCTGC GTTTCAGGCT TTCGCTATCT GTTTGAGCAG TTTCGACACA

1351         AAACTTGCTT GCGAA

AtTLP2:
polypeptide:
   1         MSLKSILRDL KEVRDGLGGI SKRSWSKSSH IAPDQTTPPL DNIPQSPWAS   (SEQ ID NO: 2)

51         LPPELLHDII WRVEESETAW PARAAVVSCA SVCKSWRGIT MEIVRIPEQC

101         GKLTFPISLK QPGPRDSPIQ CFIKRNRATA TYILYYGLMP SETENDKLLL

151         AARRIRRATC TDFIISLSAK NFSRSSSTYV GKLRSGFLGT KFTIYDNQTA

201         SSTAQAQPNR RLHPKQAAPK LPTNSSTVGN ITYELNVLRT RGPRRMHCAM

251         DSIPLSSVIA EPSVVQGIEE EVSSSPSPKG ETITTDKEIP DNSPSLRDQP

301         LVLKNKSPRW HEQLQCWCLN FKGRVTVASV KNFQLVAEID ASLDAPPEEH

351         ERVILQFGKI GKDIFTMDYR YPLSAFQAFA ICISSFDTKP ACEG cDNA:
   1         ATGTCTTTGA AAAGCATCCT TCGTGATCTG AAGGAAGTGA GGGATGGACT   (SEQ ID NO: 13)

51         TGGAGGCATC TCCAAGAGAA GCTGGTCAAA GTCGTCTCAC ATTGCTCCTG

101         ATCAAACAAC TCCACCACTG GATAACATAC CACAGAGCCC ATGGGCTTCT

151         TTGCCGCCTG AGTTGCTTCA TGACATTATC TGGAGGGTTG AAGAGAGTGA

201         GACAGCTTGG CCCGCTCGAG CTGCCGTTGT CTCTTGTGCT TCAGTATGTA

251         AATCATGGAG AGGAATCACT ATGGAGATTG TGAGGATCCC TGAGCAGTGT

301         GGGAAGCTCA CTTTTCCAAT CTCATTGAAA CAGCCGGGGC CTCGAGACTC

351         TCCAATTCAA TGTTTTATTA AGAGGAACAG AGCAACAGCT ACATACATTC

401         TCTATTATGG TTTGATGCCT TCGGAGACTG AGAACGACAA ACTGTTGTTA

451         GCAGCAAGAA GGATTAGAAG AGCGACATGC ACAGACTTTA TAATCTCCCT

501         ATCTGCAAAG AACTTCTCAC GGAGCAGCAG TACTTATGTT GGCAAATTAA

551         GGTCTGGTTT TCTGGGAACC AAGTTCACAA TATATGACAA CCAAACAGCA

601         TCATCCACAG CACAAGCCCA ACCTAACCGA AGACTCCACC CGAAACAAGC

651         GGCTCCTAAA CTACCTACGA ATAGCTCTAC CGTAGGAAAC ATAACCTACG

701         AGCTCAATGT TCTTCGCACA AGGGGACCTA GAAGAATGCA CTGCGCTATG

751         GATTCTATAC CCCTCTCTTC TGTTATTGCT GAACCGTCAG TAGTTCAAGG

801         CATAGAAGAG GAAGTCTCTT CCTCTCCTTC ACCAAAAGGA GAAACCATCA

851         CAACAGACAA AGAGATTCCT GATAATTCTC CAAGCTTAAG GGACCAACCG
```

```
 901    CTAGTTCTCA AAAACAAATC CCCAAGATGG CATGAGCAGT TGCAGTGCTG
 951    GTGCCTCAAC TTCAAGGGAA GAGTGACTGT GGCTTCAGTT AAGAATTTCC
1001    AGCTTGTTGC AGAGATTGAC GCTTCTTTGG ATGCGCCGCC TGAAGAACAT
1051    GAGAGGGTGA TCTTACAGTT TGGCAAAATC GGTAAGGATA TTTTCACCAT
1101    GGATTATCGC TACCCTCTAT CTGCTTTTCA AGCCTTTGCT ATATGCATTA
1151    GCAGCTTTGA CACCAAACCG GCATGTGAAG GG
```

AtTLP3:
polypeptide:
```
   1    MSFKSLIQDM RGELGSISRK GFDVRFGYGR SRSQRVVQDT SVPVDAFKQS  (SEQ ID NO: 3)
  51    CWASMPPELL RDVLMRIEQS EDTWPSRKNV VSCAGVCRNW REIVKEIVRV
 101    PELSSKLTFP ISLKQPGPRG SLVQCYIMRN RSNQTYYLYL GLNQAASNDD
 151    GKFLLAAKRF RRPTCTDYII SLNCDDVSRG SNTYIGKLRS NFLGTKFTVY
 201    DAQPTNPGTQ VTRTRSSRLL SLKQVSPRIP SGNYPVAHIS YELNVLGSRG
 251    PRRMQCVMDA IPASAVEPGG TAPTQTELVH SNLDSFPSFS FFRSKSIRAE
 301    SLPSGPSSAA QKEGLLVLKN KAPRWHEQLQ CWCLNFNGRV TVASVKNFQL
 351    VAAPENGPAG PEHENVILQF GKVGKDVFTM DYQYPISAFQ AFTICLSSFD
 401    TKIACE
``` cDNA:
```
   1    ATGTCCTTCA AGAGTCTCAT TCAGGACATG AGAGGAGAGC TTGGGAGTAT  (SEQ ID NO:14)
  51    ATCCAGAAAG GGATTCGATG TCAGATTCGG GTATGGTAGA TCCAGGTCTC
 101    AACGTGTTGT TCAGGATACT TCTGTTCCTG TTGATGCTTT CAAGCAGAGC
 151    TGCTGGGCTA GTATGCCTCC GGAGCTCCTG AGAGATGTTC TTATGAGGAT
 201    TGAGCAATCC GAAGACACTT GGCCGTCTAG GAAAAATGTT GTTTCTTGCG
 251    CTGGTGTCTG CAGGAACTGG CGAGAAATCG TCAAAGAGAT CGTCAGAGTT
 301    CCTGAGCTTT CTAGCAAAACT CACTTTTCCT ATCTCCCTCA AACAGCCGGG
 351    TCCTAGAGGA TCACTTGTTC AATGCTATAT TATGAGAAAC CGCAGCAATC
 401    AAACCTACTA TCTATACCTC GGGTTAAACC AAGCAGCTTC AAATGATGAT
 451    GGAAAGTTCC TTCTTGCTGC CAAGAGGTTT CGGAGGCCAA CTTGCACTGA
 501    CTACATCATC TCCTTAAACT GCGATGATGT CTCTCGAGGA AGCAATACCT
 551    ATATCGGAAA GCTTAGATCT AACTTTCTGG GACCAAGTT CACTGTCTAT
 601    GACGCTCAGC CGACGAATCC TGGAACTCAG GTTACCAGAA CCCGTTCAAG
 651    CAGACTTCTC AGTTTGAAAC AAGTGAGCCC GAGAATTCCA TCTGGCAACT
 701    ATCCTGTAGC ACATATCTCA TATGAGCTTA ACGTCTTGGG TTCCAGAGGA
 751    CCGAGGAGGA TGCAGTGTGT CATGGATGCC ATCCCTGCAT CAGCTGTAGA
 801    ACCTGGAGGA ACAGCTCCAA CTCAGACGGA ACTTGTCCAT AGCAATCTTG
 851    ATAGTTTCCC CTCATTCTCC TTCTTCAGGT CGAAATCAAT TCGTGCAGAG
 901    AGTCTCCCTT CTGGTCCATC ATCTGCTGCT CAGAAGGAAG GACTGCTTGT
 951    CCTGAAAAAC AAAGCGCCCA GATGGCACGA ACAGCTCCAG TGCTGGTGCC
1001    TCAACTTCAA TGGGAGAGTC ACAGTTGCTT CCGTCAAAAA CTTTCAGCTG
1051    GTAGCTGCTC CTGAGAATGG ACCTGCAGGA CCTGAGCACG AAAACGTGAT
1101    TCTCCAGTTT GGAAAAGTCG GAAAAGATGT GTTCACAATG GATTATCAGT
```

-continued

```
1151       ACCCTATCTC TGCCTTCCAG GCCTTCACCA TTTGCCTCAG CAGTTTCGAC
1201       ACCAAGATAG CATGTGAA
```

AtTLP4:
polypeptide:
```
  1        MPPELLRDVL MRIERSEDTW PSRKNVVSCV GVCKNWRQIF KEIVNVPEVS  (SEQ ID NO:4)
 51        SKFTFPISLK QPGPGGSLVQ CYVKRNRSNQ TFYLYLGGEA KIFCQSEPSD
101        IYLVPYSYRE THCVMDAISA SAVKPGGTAT TQTELDNFVS FRSPSGQKEG
151        VLVLKSKVPR LEEQSWCLDF NGSPENEPEN ENDIFQFAKV GNLHKLFSLY
201        EAEWIPLVRT SVFAVIARVC RDKKHTPSYE LKLALYFAKN SAILKKFVLR
251        GYTREEDLLA LPVAN
```
cDNA:
```
  1        ATGCCTCCTG AGCTTCTGAG AGATGTTCTG ATGAGGATAG AGCGATCCGA  (SEQ ID NO:15)
 51        AGACACTTGG CCTTCTAGGA AGAATGTTGT TCTTGTGTA GGTGTGTGTA
101        AGAACTGGCG ACAAATATTC AAAGAGATCG TTAACGTTCC TGAGGTTTCT
151        AGCAAATTCA CTTTTCCAAT CTCCTTGAAA CAGCCTGGTC AGGAGGATC
201        ACTTGTTCAA TGCTATGTTA AGAGAAACCG TAGCAATCAA ACTTTCTATC
251        TATACCTTGG AGGTGAAGCA AAAATATTTT GTCAGTCTGA ACCAACTGAT
301        ATTTATCTCG TTCCTTACAG TTACAGAGAG ACGCATTGCG TCATGGATGC
351        CATCTCTGCA TCAGCAGTAA AACCTGCAGG AACAGCTACA ACTCAGACAG
401        AACTCGATAA TTTCGTGTCA TTCAGGTCTC CTTCTGGTCA AAAGGAAGGA
451        GTGCTTGTTC TTAAGAGCAA AGTGCCTAGA TTGGAAGAAC AGAGCTGGTG
501        TCTCGACTTC AATGGCTCTC CTGAGAACGA ACCTGAGAAT GAAAACGACA
551        TTTTCCAGTT TGCGAAAGTC GGAAACTTGC ACAAACTCTT CAGTTTATAT
601        GACCCTGAAT GCATTCCTCT CGTTCGCACC TCAGTGTTTG CTGTCATTGC
651        TCGAGTTTGT AGAGATAAAA AGCATACACC ATCGTATGAA TTGAAACTTG
701        CATTGTACTT TGCAAAAAAC TCTGCAATCC TCAAGAAATT CGTTCTCCGC
751        GGTTACACTC GAGAAGAAGA TTTACTCGCA TTGCCCGTGG CTAAC
```

AtTLP5:
polypeptide:
```
  1        MSFLSIVRDV RDTVGSFSRR SFDVRVSNGT THQRSKSHGV EAHIEDLIVI  (SEQ ID NO: 5)
 51        KNTRWANLPA ALLRDVMKKL DESESTWPAR KQVVACAGVC KTWRLMCKDI
101        VKSPEFSGKL TFPVSLKQPG PRDGIIQCYI KRDKSNMTYH LYLSLSPAIL
151        VESGKFLLSA KRSRRATYTE YVISMDADNI SRSSSTYIGK LKSNFLGTKF
201        IVYDTAPAYN SSQILSPPNR SRSFNSKKVS PKVPSGSYNI AQVTYELNLL
251        GTRGPRRMNC IMHSIPSLAL EPGGTVPSQP EFLQRSLDES FRSIGSSKIV
301        NHSGDFTRPK EEEGKVRPLV LKTKPPRWLQ PLRCWCLNFK GRVTVASVKN
351        FQLMSAATVQ PGSGSDGGAL ATRPSLSPQQ PEQSNHDKII LHFGKVGKDM
401        FTMDYRYPLS AFQAFAISLS TFDTKLACE
```
cDNA:
```
  1        ATGTCGTTTC TGAGTATTGT TCGTGATGTT AGAGATACTG TAGGAAGCTT  (SEQ ID NO: 16)
 51        TTCGAGACGT AGTTTCGACG TGAGAGTATC TAATGGGACG ACTCATCAGA
101        GGAGTAAATC TCACGGTGTT GAGGCACATA TTGAAGATCT TATTGTAATC
151        AAGAACACTC GTTGGGCTAA TTTACCGGCT GCGCTATTAC GAGATGTGAT
```

-continued

```
 201        GAAAAAGTTG GATGAAAGCG AGAGTACTTG GCCTGCACGT AAACAAGTCG
 251        TTGCTTGTGC TGGTGTCTGC AAGACATGGA GACTAATGTG CAAAGATATT
 301        GTGAAAAGTC CTGAGTTCTC AGGCAAACTC ACATTTCCAG TTTCGTTGAA
 351        ACAGCCCGGG CCTAGGGATG GAATCATACA ATGTTATATC AAAAGAGACA
 401        AGTCTAACAT GACTTACCAC CTTTACCTTT CTCTTAGTCC TGCCATACTT
 451        GTTGAAAGTG GGAAGTTTCT TCTCTCGGCA AAGCGCTCAC GGAGAGCTAC
 501        ATACACAGAG TATGTAATAT CAATGGATGC AGACAACATT TCAAGATCAA
 551        GCAGCACTTA CATTGGCAAA CTGAAGTCTA ACTTTCTAGG GACAAAATTT
 601        ATAGTATATG ATACGGCTCC TGCGTACAAC AGTAGCCAGA TATTGTCCCC
 651        ACCAAACCGG AGTCGTAGTT TCAACTCCAA GAAAGTGTCT CCCAAAGTCC
 701        CTTCTGGAAG TTACAACATT GCTCAAGTTA CATACGAGCT GAACTTGCTT
 751        GGAACCCGTG GACCTCGTAG AATGAACTGC ATTATGCACT CTATCCCCTC
 801        CTTAGCTCTA GAACCCGGAG GTACTGTCCC TAGCCAACCT GAGTTTCTAC
 851        AACGTTCCCT TGATGAATCT TTCCGCAGCA TCCGTTCCTC AAAGATAGTC
 901        AACCACTCGG GAGATTTCAC CCGACCGAAA GAGGAAGAAG GAAAGGTGCG
 951        ACCTTTGGTA CTGAAAACTA AACCGCCAAG GTGGCTCCAA CCGTTGCGAT
1001        GTTGGTGCCT TAACTTCAAA GGGAGAGTGA CTGTAGCTTC TGTCAAGAAC
1051        TTCCAGTTGA TGTCCGCTGC AACGGTTCAG CCCGGTAGTG GTAGTGATGG
1101        TGGAGCATTG GCTACGAGGC CATCGTTATC ACCACAGCAG CCAGAGCAAT
1151        CAAACCATGA TAAGATAATA CTACACTTTG GGAAAGTGGG TAAGGATATG
1201        TTCACTATGG ACTATCGTTA TCCTCTCTCT GCCTTTCAAG CGTTTGCCAT
1251        TTCCCTGAGC ACCTTTGATA CTAAATTGGC ATGTGAA
AtTLP6:
polypeptide:
   1        MSLKNIVKNK YKAIGRRGRS HIAPEGSSVS SSLSTNEGLN QSIWVDLPPE   (SEQ ID NO:6)
  51        LLLDIIQRIE SEQSLWPGRR DVVACASVCK SWREMTKEVV KVPELSGLIT
 101        FPISLRQPGP RDAPIQCFIK RERATGIYRL YLGLSPALSG DKSKLLLSAK
 151        RVRRATGAEF VVSLSGNDFS RSSSNYIGKL RSNFLGTKFT VYENQPPPFN
 201        RKLPPSMQVS PWVSSSSSSY NIASILYELN VLRTRGPRRM QCIMHSIPIS
 251        AIQEGGKIQS PTEFTNQGKK KKKPLMDFCS GNLGGESVIK EPLILKNKSP
 301        RWHEQLQCWC LNFKGRVTVA SVKNFQLVAA AAEAGKNMNI PEEEQDRVIL
 351        QFGKIGKDIF TMDYRYPISA FQAFAICLSS FDTKPVCE
cDNA:
   1        ATGTCATTGA GAACATAGT GAAGAACAAA TACAAAGCTA TTGGTAGAAG    (SEQ ID NO:17)
  51        AGGGAGGTCA CACATTGCAC CAGAAGGATC ATCTGTGTCT TCTTCTTTAT
 101        CAACTAATGA AGGTTTAAAC CAGAGTATTT GGGTTGATTT GCCTCCAGAG
 151        TTACTTCTTG ATATAATCCA AAGGATTGAG TCTGAACAGA GTTTATGGCC
 201        GGGGAGGAGA GATGTTGTTG CTTGTGCTTC GGTTTGTAAG TCATGGAGGG
 251        AGATGACTAA AGAAGTTGTT AAAGTTCCTG AGCTCTCTGG TTTGATCACG
 301        TTTCCGATTT CTTTAAGACA GCCTGGACCT AGAGATGCTC CAATTCAATG
 351        CTTTATTAAA CGTGAAAGAG CTACGGGGAT ATACCGTCTC TATCTTGGTT
 401        TAAGCCCTGC TCTTTCCGGT GACAAGAGTA AGTTGTTGTT ATCTGCAAAG
```

-continued

```
 451  AGAGTCAGGA GAGCGACGGG TGCGGAGTTT GTTGTATCGT TATCGGGGAA
 501  TGACTTCTCG AGAAGTAGTA GTAATTACAT AGGAAAACTG AGATCAAATT
 551  TCCTGGGAAC GAAGTTCACA GTCTACGAAA ACCAACCTCC TCCGTTTAAC
 601  CGAAAGCTCC CACCATCGAT GCAAGTGTCT CCATGGGTAT CGTCGTCATC
 651  TAGTAGTTAC AACATAGCTT CAATCTTGTA TGAGCTGAAT GTTCTGAGAA
 701  CCAGAGGTCC AAGAAGAATG CAATGTATAA TGCACAGTAT CCCGATTTCA
 751  GCGATTCAAG AAGGCGGCAA AATCCAGTCG CCAACGGAGT TCACAAACCA
 801  AGGAAAGAAG AAGAAGAAGC CGCTGATGGA TTTCTGCTCA GGGAACCTGG
 851  GAGGAGAATC CGTTATAAAA GAACCATTAA TTCTGAAAAA CAAGTCGCCG
 901  AGATGGCACG AACAGCTTCA GTGCTGGTGT CTAAACTTCA AAGGTCGAGT
 951  CACAGTCGCC TCGGTGAAAA ACTTCCAGCT AGTGGCAGCT GCTGCAGAAG
1001  CAGGGAAGAA CATGAACATA CCAGAAGAGG AACAAGATAG AGTGATATTA
1051  CAGTTTGGGA AGATAGGCAA AGACATTTTC ACAATGGATT ATCGTTACCC
1101  GATCTCTGCA TTCCAAGCTT TTGCTATTTG TTTAAGCAGC TTCGACACGA
1151  AGCCAGTCTG CGAA
```

AtTLP7:
polypeptide:
```
  1  MPLSRSLLSR RISNSFRFHQ GETTTAPESE SIPPPSNMAG SSSWSAMLPE  (SEQ ID NO:7)
 51  LLGEIIRRVE ETEDRWPQRR DVVTCACVSK KWREITHDFA RSSLNSGKIT
101  FPSCLKLPGP RDFSNQCLIK RNKKTSTFYL YLALTPSFTD KGKFLLAARR
151  FRTGAYTEYI ISLDADDFSQ GSNAYVGKLR SDFLGTNFTV YDSQPPHNGA
201  KPSNGKASRR FASKQISPQV PAGNFEVGHV SYKFNLLKSR GPRRMVSTLR
251  CPSPSPSSSS AGLSSDQKPC DVTKIMKKPN KDGSSLTILK NKAPRWHEHL
301  QCWCLNFHGR VTVASVKNFQ LVATVDQSQP SGKGDEETVL LQFGKVGDDT
351  FTMDYRQPLS AFQAFAICLT SFGTKLACE
``` cDNA:
```
  1  ATGCCTTTGT CACGGTCCCT CCTTTCGCGG AGGATCTCGA ACTCTTTTAG  (SEQ ID NO:18)
 51  GTTTCATCAG GGAGAGACAA CGACGGCACC GGAATCCGAA TCGATTCCTC
101  CGCCGTCGAA TATGGCCGGT TCTTCGTCAT GGTCGGCGAT GCTCCCTGAA
151  TTATTAGGCG AGATCATTCG TCGCGTGGAG GAGACTGAGG ACCGTTGGCC
201  TCAACGTCGT GATGTAGTTA CTTGCGCTTG CGTTTCTAAG AAATGGAGAG
251  AAATCACTCA CGATTTCGCT AGATCCTCTC TTAACTCTGG CAAAATTACT
301  TTCCCTTCTT GCCTCAAATT GCCAGGTCCT AGAGACTTTT CTAATCAGTG
351  CTTGATAAAG AGGAACAAGA AGACATCAAC GTTTTACTTG TATCTTGCTC
401  TAACACCATC ATTCACTGAT AAGGGAAAGT TCTTCTGGC GGCGCGGAGG
451  TTTAGGACCG GTGCTTACAC TGAGTACATC ATATCACTTG ATGCTGATGA
501  TTTCTCTCAA GGAAGTAATG CCTACGTCGG AAAATTAAGA TCAGATTTTC
551  TTGGGACCAA CTTTACAGTA TACGATAGCC AACCACCACA CAACGGAGCA
601  AAACCTTCAA ATGGCAAAGC CAGTCGCAGA TTTGCATCAA AGCAGATAAG
651  CCCTCAAGTT CCAGCAGGCA ACTTTGAAGT CGGTCATGTT TCTTATAAAT
701  TCAACCTTTT GAAATCAAGA GGTCCAAGAA GAATGGTAAG CACACTCCGA
```

```
-continued
 751    TGCCCATCAC CATCACCTTC ATCATCATCC GCTGGACTCT CGTCTGACCA

801    AAAGCCATGT GATGTAACCA AGATAATGAA AAAACCCAAC AAGGATGGTT

851    CCAGCTTGAC AATACTAAAG AACAAAGCTC CTAGATGGCA CGAGCACTTG

901    CAGTGCTGGT GTCTGAACTT CCATGGACGA GTTACTGTTC CTTCGGTCAA

951    GAACTTTCAG CTGGTTGCGA CCGTTGACCA AAGTCAACCG AGCGGTAAAG

1001    GCGATGAAGA AACAGTTCTT CTACAGTTTG GTAAAGTGGG AGATGACACT

1051    TTCACTATGG ATTATAGACA GCCTCTCTCT GCATTTCAGG CTTTTGCTAT

1101    CTGTCTCACA AGTTTCGGCA CTAAACTTGC CTGCGAG

AtTLP8:
polypeptide:
   1   MAGSRKVNDL LEENKGNVDT ITGSLSTQKG EDKENVSPEK VSTSVETRKL   (SEQ ID NO:8)

51   DRALKSQSMK GNSGFPTEVT NFKSFSTGGR TALKQSSLQA CMQKNSEVDK

101   SSFGMKTWTS VDSEHSSSLK VWEFSDSEAA PASSWSTLPN RALLCKTLPL

151   DVGRCTCLIV KEQSPEGLSH GSVYSLYTHE GRGRKDRKLA VAYHSRRNGK

201   SIFRVAQNVK GLLCSSDESY VGSMTANLLG SKYYIWDKGV RVGSVGKMVK

251   PLLSVVIFTP TITTWTGSYR RMRTLLPKQQ PMQKNNNKQV QQASKLPLDW

301   LENKEKIQKL CSRIPHYNKI SKQHELDFRD RGRTGLRIQS SVKNFQLTLT

351   ETPRQTILQM GRVDKARYVI DFRYPFSGYQ AFCICLASID SKLCCTV cDNA:
   1   ATGGCTGGTT CGAGAAAAGT GAATGATTTG TTGGAGGAAA ATAAGGGAAA   (SEQ ID NO:19)

51   TGTGGACACA ATTACAGGGT CTTTATCCAC TCAAAAGGGA GAGGATAAGG

101   AGAATGTGTC GCCGGAGAAA GTCTCTACCT CTGTGGAAAC TCGGAAACTA

151   GATCGAGCTT TGAAGTCTCA ATCGATGAAG GGTAACTCTG GGTTTCCAAC

201   GGAAGTTACA AATTTCAAAT CTTTCTCAAC TGGTGGTCGA ACAGCTCTGA

251   AGCAGTCATC ACTGCAAGCG TGTATGCAGA AGAACAGTGA GGTTGATAAG

301   AGTAGTTTCG GAATGAAAAC TTGGACTAGT GTTGATTCAG AGCATTCAAG

351   TTCGTTGAAA GTGTGGGAGT TTTCGGATTC TGAAGCTGCC CCTGCTTCCT

401   CTTGGTCTAC TTTGCCCAAC AGGGCTTTGT TGTGCAAGAC ACTACCTTTG

451   GATGTGGGAA GATGCACTTG TCTGATTGTG AAAGAACAAT CACCTGAAGG

501   CTTGAGCCAC GGATCTGTAT ATTCACTTTA TACACATGAA GGTCGGGGGC

551   GTAAAGACCG GAAGTTAGCA GTTGCTTACC ATAGCCGACG TAATGGGAAA

601   TCTATATTTA GGGTGGCACA GAATGTTAAG GGATTGCTGT GCAGTTCGGA

651   TGAAAGTTAT GTCGGTTCCA TGACGGCTAA TCTCTTGGGT TCCAAGTACT

701   ACATATGGGA CAAGGGAGTT CGAGTTGGTT CTGTAGGTAA ATGGTGAAG

751   CCGCTTCTTT CGGTTGTAAT ATTCACACCC ACCATAACAA CTTGGACAGG

801   GAGCTACAGA AGAATGAGAA CTTTGCTACC AAAGCAGCAG CCAATGCAGA

851   AAAACAACAA TAAGCAGGTT CAACAAGCTA GTAAACTACC GCTTGATTGG

901   CTTGAGAATA AGGAAAAAAT TCAGAAGCTA TGCTCAAGGA TACCACATTA

951   CAACAAAATC TCCAAGCAGC ATGAGTTAGA CTTCAGAGAC AGAGGAAGAA

1001   CAGGACTGAG AATACAGAGC TCGGTGAAGA ACTTTCAGCT AACACTCACG

1051   GAGACTCCAA GGCAGACAAT TCTTCAAATG GGGAGAGTTG ACAAAGCAAG
```

-continued

```
1101        ATATGTAATC GACTTCAGGT ATCCATTCTC AGGCTACCAA GCATTCTGCA
1151        TTTGCTTGGC TTCTATTGAT TCCAAGCTTT GTTGTACTGT T
```

AtTLP9:
polypeptide:
```
  1         MTFRSLLQEM RSRPHRVVHA AASTANSSDP FSWSELPEEL LREILIRVET    (SEQ ID NO:9)
 51         VDGGDWPSRR NVVACAGVCR SWRILTKEIV AVPEFSSKLT FPISLKQSGP
101         RDSLVQCFIK RNRNTQSYHL YLGLTTSLTD NGKFLLAASK LKRATCTDYI
151         ISLRSDDISK RSNAYLGRMR SNFLGTKFTV FDGSQTGAAK MQKSRSSNFI
201         KVSPRVPQGS YPIAHISYEL NVLGSRGPRR MRCIMDTIPM SIVESRGVVA
251         STSISSFSSR SSPVFRSHSK PLRSNSASCS DSGNNLGDPP LVLSNKAPRW
301         HEQLRCWCLN FHGRVTVASV KNFQLVAVSD CEAGQTESRI ILQFGKVGKD
351         MFTMDYGYPI SAFQAFAICL SSFETRIACE
``` cDNA:
```
  1         ATGACGTTCC GAAGTTTACT CCAGGAAATG CGGTCTAGGC CACACCGTGT    (SEQ ID NO:20)
 51         AGTTCACGCC GCCGCCTCAA CCGCTAATAG TTCAGACCCT TTCAGCTGGT
101         CGGAGCTCCC GGAGGAGCTG CTTAGAGAAA TCCTGATTAG GGTTGAGACT
151         GTTGACGGCG GCGATTGGCC GTCGCGGCGA AACGTGGTGG CTTGTGCCGG
201         CGTTTGTCGT AGCTGGAGGA TTCTCACCAA GGAGATTGTA GCTGTTCCTG
251         AATTCTCCTC TAAATTGACT TTCCCTATCT CCCTCAAGCA GTCTGGTCCA
301         AGAGATTCTC TAGTTCAATG CTTTATAAAA CGTAATCGAA ATACTCAATC
351         GTATCATCTC TATCTCGGAT TAACTACCTC TTTGACGGAT AACGGGAAGT
401         TTCTTCTTGC TGCTTCTAAG CTGAAGCGCG CAACTTGCAC TGATTACATC
451         ATCTCTTTGC GTTCAGACGA TATCTCAAAG AGAAGCAACG CGTATCTTGG
501         GAGAATGAGA TCGAACTTCC TTGGAACAAA ATTCACGGTC TTTGATGGTA
551         GTCAGACCGG AGCAGCGAAG ATGCAGAAGA GCCGCTCTTC TAATTTCATC
601         AAAGTTTCAC CTAGAGTTCC TCAGGGAAGT TACCCCATCG CTCACATTTC
651         ATACGAGTTA AACGTCTTAG GCTCTCGGGG ACCGAGAAGA ATGCGTTGCA
701         TCATGGATAC AATACCTATG AGCATCGTGG AGTCGCGAGG AGTAGTAGCT
751         TCAACATCCA TAAGCTCTTT TTCCAGTCGG TCATCACCAG TCTTTAGGTC
801         TCACTCAAAA CCATTGCGCA GTAATAGTGC ATCATGTAGC GACTCAGGCA
851         ACAACCTGGG AGATCCACCA TTGGTGCTGA GCAACAAAGC TCCACGGTGG
901         CATGAGCAGT TACGTTGCTG GTGCTTAAAT TTCCATGGTC GAGTCACAGT
951         GGCTTCGGTT AAGAACTTTC AGCTTGTGGC AGTTAGTGAC TGTGAAGCAG
1001        GGCAGACATC TGAGAGGATC ATACTCCAGT TTGGGAAAGT TGGGAAGGAC
1051        ATGTTTACCA TGGATTATGG ATATCCGATT TCTGCGTTTC AAGCGTTTGC
1101        TATCTGCCTG AGCAGTTTTG AAACCAGAAT TGCCTGTGAA
```

AtTLP10:
polypeptide:
```
  1         MSFRGIVQDL RDGFGSLSRR SFDFRLSSLH KGKAQGSSFR EYSSSRDLLS    (SEQ ID NO:10)
 51         PVIVQTSRWA NLPPELLFDV IKRLEESESN WPARKHVVAC ASVCRSWRAM
101         CQEIVLGPEI CGKLTFPVSL KQPGPRDAMI QCFIKRDKSK LTFHLFLCLS
151         PALLVENGKF LLSAKRTRRT TRTEYIISMD ADNISRSSNS YLGKLRSNFL
```

```
201         GTKFLVYDTQ PPPNTSSSAL ITDRTSRSRF HSRRVSPKVP SGSYNIAQIT

251         YELNVLGTRG PRRMHCIMNS IPISSLEPGG SVPNQPEKLV PAPYSLDDSF

301         RSNISFSKSS FDHRSLDFSS SRFSEMGISC DDNEEEASFR PLILKNKQPR

351         WHEQLQCWCL NFRGRVTVAS VKNFQLVAAR QPQPQGTGAA AAPTSAPAHP

401         EQDKVILQFG KVGKDMFTMD YRYPLSAFQA FAICLSSFDT KLACE cDNA:
  1         ATGTCGTTTC GAGGCATTGT TCAAGATTTG AGAGATGGGT TGGGAGCTTT    (SEQ ID NO:21)

51         GTCAAGGAGG AGTTTCGATT TTAGGCTCTC GAGTCTTCAT AAAGGGAAAG

101         CTCAGGGTTC TTCGTTCCGT GAGTATTCGT CATCCCGTGA TCTCTTGTCG

151         CCTGTGATAG TTCAGACAAG TAGATGGGCT AATCTTCCTC CAGAGTTACT

201         CTTTGATGTG ATCAAAAGAT TAGAGGAAAG TGAGAGTAAT TGGCCTGCAA

251         GAAAACATGT TGTGGCTTGT GCTTCGGTTT GTCGGTCTTG GAGAGCTATG

301         TGCCAAGAGA TTGTTTTGGG GCCTGAAATC TGTGGGAAAC TCACTTTCCC

351         TGTTTCCCTC AAACAGCCAG GGCCTCGTGA TGCAATGATT CAGTGTTTCA

401         TCAAAAGGGA TAAATCAAAG CTAACATTTC ACCTTTTTCT TTGTTTAAGT

451         CCCGCTCTAT TAGTGGAGAA TGGGAAATTT CTTCTTTCAG CTAAAAGAAC

501         TCGTAGAACT ACTCGAACCG AGTACATTAT CTCCATGGAT GCTGATAACA

551         TCTCAAGATC CAGCAACTCT TACCTCGGAA AGCTCAGATC AAACTTCCTT

601         GGGACAAAGT TCTTGGTGTA CGACACGCAA CCACCACCAA ACACATCTTC

651         GAGCGCACTT ATCACTGATC GAACAAGCCG AAGCAGGTTT CACTCCAGAC

701         GAGTTTCTCC TAAAGTACCA TCCGGAAGCT ACAACATTGC TCAAATCACC

751         TATGAGCTCA ACGTGTTGGG CACACGCGGG CCACGACGAA TGCACTGCAT

801         CATGAACTCC ATCCCAATTT CATCGCTCGA ACCAGGCGGT TCAGTCCCTA

851         ACCAACCCGA GAAACTCGTC CTGCACCAT ACTCTCTCGA CGACTCATTC

901         CGCAGTAACA TCTCCTTCTC CAAATCATCA TTTGACCACC GCTCCCTCGA

951         TTTCAGCAGT TCTAGATTCT CCGAAATGGG AATATCCTGC GACGACAACG

1001        AAGAAGAAGC GAGTTTCAGA CCGTTGATTC TAAAGAACAA GCAGCCAAGG

1051        TGGCACGAGC AGTTGCAATG CTGGTGTTTG AATTTCCGCG ACGTGTGAC

1101        AGTTGCATCG GTTAAGAATT TCCAGCTTGT AGCAGCAAGA CAGCCGCAGC

1151        CTCAAGGGAC AGGTGCAGCA GCAGCACCAA CAAGTGCACC TGCTCACCCT

1201        GAGCAAGACA AGGTGATTCT CCAGTTTGGT AAAGTAGGGA AAGATATGTT

1251        CACAATGGAC TATAGGTATC CATTATCGGC GTTCAGGCG TTTGCGATAT

1301        GCTTAAGCAG CTTTGACACC AAGCTTGCTT GTGAA

AtTLP11:
polypeptide:
  1         MRSRPHRVVH DLAAAAAADS TSVSSQDYRW SEIPEELLRE ILIRVEAADG    (SEQ ID NO:11)

51         GGWPSRRSVV ACAGVCRGWR LLMNETVVVP EISSKLTFPI SLKQPGPRDS

101         LVQCFIKRNR ITQSYHLYLG LTNSLTDDGK FLLAACKLKH TTCTDYIISL

151         RSDDMSRRSQ AYVGKVRSNF LGTKFTVFDG NLLPSTGAAK LRKSRSYNPA

201         KVSAKVPLGS YPVAHITYEL NVLGSRGPRK MQCLMDTIPT STMEPQGVAS

251         EPSEFPLLGT RSTLSRSQSK PLRSSSSHLK ETPLVLSNKT PRWHEQLRCW
```

-continued

```
 301       CNLFHGRVTV ASVKNFQLVA AGASCGSGTG MSPERQSERI ILQFGKVGKD

351       MFTMDYGYPI SAFQAFAICL SSFETRIACE cDNA:
   1       ATGCGTTCGA GACCGCATCG TGTGGTCCAC GACCTTGCCG CCGCCGCAGC  (SEQ ID NO:22)

51       TGCCGATTCC ACTTCTGTGT CATCGCAAGA TTATCGCTGG TCAGAGATTC

101       CTGAAGAGCT TCTTAGGGAG ATTCTGATTC GTGTTGAAGC GGCGGACGGT

151       GGCGGATGGC CGTCACGACG CAGCGTGGTG GCTTGTGCCG GCGTTTGTCG

201       TGGCTGGCGG CTACTTATGA ACGAAACCGT CGTTGTCCCT GAGATCTCTT

251       CTAAGTTGAC TTTCCCCATC TCTCTCAAGC AGCCTGGTCC AAGGGATTCA

301       CTGGTTCAAT GCTTTATCAA ACGTAATCGA ATTACGCAAT CATATCATCT

351       CTATCTCGGA TTAACCAACT CTTTAACGGA TGATGGGAAG TTTTTGCTTG

401       CTGCGTGTAA GTTGAAGCAC ACAACTTGTA CGGATTACAT TATCTCTTTA

451       CGTTCTGATG ATATGTCGAG AAGAAGCCAA GCTTATGTTG GCAAAGTGAG

501       ATCGAACTTC CTAGGAACGA AATTCACTGT CTTTGATGGA AATCTGCTGC

551       CTTCAACGGG AGCCGCAAAG TTGAGAAAGA GCCGATCTTA TAATCCCGCA

601       AAAGTTTCAG CAAAAGTTCC TCTTGGAAGT TATCCTGTCG CTCATATCAC

651       ATATGAGCTG AATGTCTTAG GATCCCGGGG ACCAAGAAAG ATGCAATGTC

701       TTATGGACAC AATACCTACA AGCACAATGG AGCCTCAAGG AGTAGCTTCA

751       GAACCATCAG AGTTTCCCTT ACTCGGTACT CGGTCAACCT TATCCAGGTC

801       TCAGTCAAAA CCATTACGCA GTAGCTCAAG CCACCTGAAA GAAACACCAT

851       TAGTGCTGAG CAACAAGACA CCACGGTGGC ACGAGCAGCT ACGCTGCTGG

901       TGCTTGAATT TCCATGGCCG TGTCACAGTA GCGTCAGTGA AGAACTTTCA

951       GCTCGTGGCA GCAGGAGCTA GCTGTGGCAG TGGCACGGGA ATGTCACCGG

1001       AGAGGCAGAG CGAGCGGATT ATATTGCAGT TTGGGAAAGT CGGGAAAGAT

1051       ATGTTCACGA TGGATTATGG ATACCCGATC TCAGCTTTCC AGGCTTTTGC

1101       CATTTGCTTG AGCAGCTTTG AGACTAGAAT CGCTTGTGAA
```

Accordingly, one aspect of the invention features an isolated polypeptide containing an amino acid sequence at least 70% (i.e., any number between 70% and 100%, inclusive) identical to one of SEQ ID NOs: 1-11. When expressed in a plant cell, e.g., an *Arabidopsis* cell, the polypeptide regulates the transcription of genes, in response to environmental stimuli. The polypeptide of the invention can be used to identify DNA elements, such as promoters, enhances, or silencers, which it binds to. Such DNA elements mediate the response of plants to various environmental factors. The polypeptide of the invention can also be used for producing anti-AtTLP antibodies (either monoclonal or polyclonal). These antibodies in turn are useful for detecting the presence and distribution of AtTLP proteins in tissues and in cellular compartments. For example, such antibodies can be used to verify the expression of TLP proteins in a transgenic plant.

An isolated polypeptide refers to a polypeptide substantially free from naturally associated molecules, i.e., it is at least 75% (i.e., any number between 75% and 100%, inclusive) pure by dry weight. Purity can be measured by any appropriate standard method, for example, by column chromatography, polyacrylamide gel electrophoresis, or HPLC analysis.

The percent identity of two amino acid sequences is determined using the algorithm of Karlin and Altschul ((1990) Proc. Natl. Acad. Sci. USA 87, 2264-2268), modified as in Karlin and Altschul ((1993) Proc. Natl. Acad. Sci. USA 90, 5873-5877). Such an algorithm is incorporated into the XBLAST programs of Altschul, et al. ((1990) J. Mol. Biol. 215, 403-410). BLAST protein searches are performed with the XBLAST program, score=50, wordlength=3. Where gaps exist between two sequences, Gapped BLAST is utilized as described in Altschul, et al. ((1997) Nucleic Acids Res. 25, 3389-3402). When employing BLAST and Gapped BLAST programs, one can conveniently use the default parameters (e.g., XBLAST). See ncbi.nlm.nih.gov.

The invention further features (1) an isolated nucleic acid encoding a polypeptide of the invention and (2) an isolated nucleic acid that, under a high stringent condition, hybridizes to a probe containing a sequence selected from the group consisting of SEQ ID NOs: 12-22, or a complement of any selected sequence. Such a nucleic acid is at least 15

(e.g., at least 30, 50, 100, 200, 500, or 1000) nucleotides in length. By hybridization under a high stringent condition is meant hybridization at 65° C., 0.5×SSC, followed by washing at 45° C., 0.1×SSC. The nucleic acids of the invention can be used to determine whether an AtTLP mRNA is expressed in a tissue or cell. The nucleic acids can be used as primers in PCR-based detection methods, or as labeled probes in nucleic acid blots (e.g., Northern blots).

An isolated nucleic acid refers to a nucleic acid the structure of which is not identical to that of any naturally occurring nucleic acid or to that of any fragment of a naturally occurring genomic nucleic acid. The term therefore covers, for example, (a) a DNA which has the sequence of part of a naturally occurring genomic DNA molecule but is not flanked by both of the coding sequences that flank that part of the molecule in the genome of the organism in which it naturally occurs; (b) a nucleic acid incorporated into a vector or into the genomic DNA of a prokaryote or eukaryote in a manner such that the resulting molecule is not identical to any naturally occurring vector or genomic DNA; (c) a separate molecule such as a cDNA, a genomic fragment, a fragment produced by polymerase chain reaction (PCR), or a restriction fragment; and (d) a recombinant nucleotide sequence that is part of a hybrid gene, i.e., a gene encoding a fusion protein.

The invention also features a vector and a host cell containing a nucleic acid of the invention. The host cell can be an *E. coli.*, a yeast, an insect, a plant (e.g., *Arabidopsis*), or a mammalian cell. The vector and host cell can be used for producing a polypeptide of the invention. For this purpose, one can culture the host cell in a medium under conditions permitting expression of the polypeptide, and isolate the polypeptide.

The just-described vector and host cell can also be used for generating a transformed plant cell or a transgenic plant containing a recombinant nucleic acid that encodes a heterologous polypeptide of SEQ ID NO: 1, 2, 3, 4, 5, 6, 7, 8, 9, 10, or 11. One can generate such a transformed plant cell by introducing into a plant cell a recombinant nucleic acid encoding such a heterologous polypeptide and expressing the polypeptide in the cell. To generate a transgenic plant, one can (1) introduce into a plant cell a recombinant nucleic acid encoding one just-described heterologous polypeptide; (2) expressing the polypeptide in the cell, and (3) cultivating the cell to generate a plant. The transformed plant cell or transgenic plant is more sensitive to environmental factors, such as high salinity, pathogens, and chilling, and therefore can be used as a sensor to detect and monitor small changes in environment, such as soil and air.

Also within the scope of this invention are a homozygous transformed plant cell (e.g., an *Arabidopsis* cell) and a transgenic plant (e.g. *Arabidopsis*) that lack a polypeptide containing a sequence of SEQ ID NO: 1, 2, 3, 4, 5, 6, 7, 8, 9, 10, or 11. The transformed plant cell or transgenic plant, compared with the wild type cell or plant, has a higher (by at least 30%, e.g., 50%, 90%, 100%, 200%) tolerance to salt, chilling, pathogens, oxidative stress, or water-deficit due to absence of or lowered level of the polypeptide. In addition, the invention features method of making the transformed plant cell and the transgenic plant. Both methods include introducing into a plant cell a nucleic acid (e.g., a T-DNA, an anti-sense RNA, and an iRNA) that decreases the expression of a gene encoding a polypeptide of SEQ ID NO: 1, 2, 3, 4, 5, 6, 7, 8, 9, 10, or 11. The method for making the plant further includes cultivating the plant cell to generate a plant.

The details of one or more embodiments of the invention are set forth in the accompanying drawings and the description below. Other features, objects, and advantages of the invention will be apparent from the description and drawings, and from the claims.

DETAILED DESCRIPTION

This invention is based on an unexpected discovery that (1) overexpression of AtTLPs in *Arabidopsis* increases sensitivity of the plant to various environmental factors, such as salt, chilling, oxidative stress, or water-deficit; and (2) lack of expression of AtTLPs increases tolerance of the plant to several environmental factors.

Accordingly, in one aspect, the invention features a transformed plant cell containing a recombinant nucleic acid that encodes a heterologous AtTLP. The AtTLP proteins useful for this invention include, *Arabidopsis* AtTLPs 1-11 and TLPs of other species. The plant cell can be a dicot plant cell (e.g., a tomato cell, a *brassica* cell, or a potato cell) or a monocot plant cell (e.g. a rice cell, a wheat cell, or a barley cell).

A transformed plant cell of the invention can be produced by introducing into a plant cell a recombinant nucleic acid that encodes a heterologous AtTLP protein and expressing the protein in the cell. Techniques for transforming a wide variety of plant cells are well known in the art and can be found in technical and scientific literature. See, for example, Weising et al., 1988, Ann. Rev. Genet. 22:421-477. To express a heterologous AtTLP gene in a plant cell, the gene can be combined with transcriptional and translational initiation regulatory sequences that direct the transcription of the gene and translation of the encoded protein in the plant cell.

For overexpression, a constitutive plant promoter may be employed. A constitutive promoter is active under most environmental conditions and states of cell differentiation. Examples of constitutive promoters include the cauliflower mosaic virus (CaMV) 35S transcription initiation region, the 1'- or 2'-promoter derived from T-DNA of *Agrobacterium tumafaciens*, the ACT11 and Cat3 promoters from *Arabidopsis* (Huang et al., 1996, Plant Mol. Biol. 33:125-139 and Zhong et al., 1996, Mol. Gen. Genet. 251:196-203), the stearoyl-acyl carrier protein desaturase gene promoter from *Brassica napus* (Solocombe et al., 1994, Plant Physiol. 104:1167-1176), and the GPc1 and Gpc2 promoters from maize (Martinez et al., 1989, J. Mol. Biol. 208:551-565 and Manjunath et al., 1997, Plant Mol. Biol. 33:97-112).

Alternatively, a tissue-specific promoter or an inducible promoter may be employed to direct expression of the AtTLP gene in a specific cell type or under more precise environmental or developmental control. Examples of environmental conditions that may affect transcription by inducible promoters include anaerobicity, elevation of temperature, presence of light, spray with chemicals or hormones, or infection by a pathogen. Examples of a tissue-specific promoter or an inducible promoter include the root-specific ANR1 promoter (Zhang and Forde, 1998, Science 279:407) and the photosynthetic organ-specific RBCS promoter (Khoudi et al., 1997, Gene 197:343).

For proper polypeptide expression, a polyadenylation region at the 3'-end of the coding region should be included. The polyadenylation region can be derived from the same gene, from a variety of other genes, or from T-DNA.

A marker gene can also be included to confer a selectable phenotype on plant cells. For example, the marker gene may encode a protein that confers biocide resistance, antibiotic resistance (e.g., resistance to kanamycin, G418, bleomycin, hygromycin), or herbicide resistance (e.g., resistance to chlorosulfuron or Basta).

A recombinant nucleic acid that encodes a heterologous AtTLP protein may be introduced into the genome of a desired plant host cell by a variety of conventional techniques. For example, the recombinant nucleic acid may be introduced directly into the genomic DNA of a plant cell using techniques such as polyethylene glycol precipitation, electroporation, microinjection, or ballistic methods (e.g., DNA particle bombardment). See, e.g., Paszkowski et al., 1984, EMBO J. 3:2717-2722, Fromm et al., 1985, Proc. Natl. Acad. Sci. USA 82:5824, and Klein et al., 1987, Nature 327:70-73. Alternatively, the recombinant nucleic acid may be combined with suitable T-DNA flanking regions and introduced into a conventional *Agrobacterium tumefaciens* host vector. The virulence functions of the *Agrobacterium tumefaciens* host direct the insertion of the AtTLP gene and adjacent marker into the plant cell DNA when the cell is infected by the bacteria. *Agrobacterium tumefaciens*-mediated transformation techniques, including disarming and use of binary vectors, are well known in the art. See, e.g., Horsch et al., 1984, Science 233:496-498; Fraley et al., 1983, Proc. Natl. Acad. Sci. USA 80:4803; and Gene Transfer to Plants, Potrykus, ed., Springer-Verlag, Berlin, 1995.

The presence and copy number of a heterologous AtTLP gene in a transgenic plant can be determined using standard methods, e.g., Southern blotting. Expression of the heterologous AtTLP gene in a transgenic plant can be confirmed by detecting and quantifying the heterologous AtTLP mRNA or protein in the transgenic plant.

The transformed plant cells thus obtained can then be cultured to regenerate a whole plant. Regeneration techniques rely on manipulation of certain phytohormones in a tissue culture growth medium, typically relying on a biocide or herbicide marker that has been introduced together with a heat shock factor gene. Plant regeneration from cultured protoplasts is described in Evans et al., Protoplasts Isolation and Culture, Handbook of Plant Cell Culture, pp. 124-176, MacMillilan Publishing Company, New York, 1983; and Binding, Regeneration of Plants, Plant Protoplasts, pp. 21-73, CRC Press, Boca Raton, 1985. Regeneration can also be obtained from plant callus, explants, organs, or parts thereof. Such regeneration techniques are described generally in Klee et al., 1987, Ann. Rev. Plant Phys. 38:467-486.

Once the heterologous AtTLP gene has been confirmed to be stably incorporated in the genome of a transgenic plant, it can be introduced into other plants by sexual crossing. Depending upon the species to be crossed, one or more standard breeding techniques can be used to generate the whole plant.

In another aspect, the invention feature a homozygous transformed plant cell that lack one or more of AtTLPs 1-11. Absence of the AtTLP(s) enhances tolerance of the cell to various environmental factors, e.g., high salinity. Such a transformed cell can be made by introducing into a plant cell a nucleic acid that lowers the expression of a gene encoding a polypeptide of SEQ ID NO: 1, 2, 3, 4, 5, 6, 7, 8, 9, 10, or 11. The nucleic acid, e.g., T-DNA, antisense RNA, or iRNA, can be introduced into the cell using one of the standard transforming techniques described above. Stable transformants can be selected using the marker genes and selection methods also described above. A whole plant can then be regenerated from the transformed plant cells. It can be further crossed using conventional breeding techniques to generate homozygous plant.

The specific example below is to be construed as merely illustrative, and not limitative of the remainder of the disclosure in any way whatsoever. Without further elaboration, it is believed that one skilled in the art can, based on the description herein, utilize the present invention to its fullest extent. All publications cited herein are hereby incorporated by reference in their entirety.

Identification of the AtTLP Family

A tubby consensus sequence (Pfam PF01167, Kleyn et al., 1996, Cell 85: 281-290 and Noben-Trauth et al., 1996, Nature 380: 534-538) was used to search the *Arabidopsis thaliana* expressed sequence tag (EST) database and the completed *Arabidopsis* genome sequence (The Institute of Genome Research, TIGR) with multiple BLAST algorithms to locate all the sequences sharing significant similarities with the tubby domain (P-value <0.0085). The search results revealed eleven TUBBY-like protein genes, termed AtTLP1 to AtTLP11, in the *Arabidopsis* genome. For each of the 11 genes, the corresponding BAC locus (The *Arabidopsis* Information Resource), Tentative Consensus (TC) group, AGI gene code, cDNA GenBank accession number, and predicted protein length (No. of amino acid) are summarized in Table 1 below.

TABLE 1

AtTLP family members

| Gene Name | BAG Locus | TC group | AGI Gene Code | cDNA GenBank Accession No. | Predicted Protein Length |
|---|---|---|---|---|---|
| AtTLP1 | F22K20.1 | TC95487 | At1g76900 | AF487267 | 455 |
| AtTLP2 | T30D6.21 | TC86308 | At2g18280 | AY045773 | 394 |
| AtTLP3 | F17A22.29 | TC86633 | At2g47900 | AY045774 | 406 |
| AtTLP4 | F8K4.13 | — | At1g61940 | — | 265 |
| AtTLP5 | T10P12.9 | TC102456 | At1g43640 | AY046921 | 429 |
| AtTLP6 | F8G22.1 | TC90700 | At1g47270 | AF487268 | 388 |
| AtTLP7 | F12M16.22 | TC88599 | At1g53320 | AY092403 | 379 |
| AtTLP8 | T24D18.17 | — | At1g16070 | AF487269 | 397 |
| AtTLP9 | F24P17.15 | TC102624 | At3g06380 | AF487270 | 380 |
| AtTLP10 | F4F7.13. | TC101291 | At1g25280 | AF487271 | 445 |
| AtTLP11 | T1A4.60 | — | At5g18680 | AY046922 | 380 |

Gene-specific 5' and 3' primers were designed based on the sequence of the predicted open reading frame (ORF) and the corresponding EST in the database. The primer pairs used are listed below:

```
AtTLP1-5' (5'-ATGTCGTTCCGTAGCATAGTTCGT-3')
(SEQ ID NO:23)

AtTLP1-3' (5'-TTATTCGCAAGCAAGTTTTGTGTCG-3')
(SEQ ID NO:24)

AtTLP2-5' (5'-ATGTCTTTGAAAAGCATCCTTCGTGATC-3')
(SEQ ID NO:25)

AtTLP2-3' (5'-TTACCCTTCACATGCCGGTTTGGTGTCA-3')
(SEQ ID NO:26)

AtTLP3-5' (5'-ATGTCCTTCAAGAGTCTCATTCAG-3')
(SEQ ID NO:27)

AtTLP3-3' (5'-TCATTCACATGCTATCTTGGTGTC-3')
(SEQ ID NO:28)

AtTLP5-5' (5'-ATGTCGTTTCTGAGTATTGTTCG-3')
(SEQ ID NO:29)

AtTLP5-3' (5'-TTATTCACATGCCAATTTAGTAT-3')
(SEQ ID NO:30)

AtTLP6-5' (5'-ATGTCATTGAAGAACATAGTGAA-3')
(SEQ ID NO:31)

AtTLP6-3' (5'-TCATTCGCAGACTGGCTTCGTGT-3')
(SEQ ID NO:32)

AtTLP7-5' (5'-ATGCCTTTGTCACGGTCCCTC-3')
(SEQ ID NO:33)

AtTLP7-3' (5'-TCACTCGCAGGCAAGTTTAGTG-3')
(SEQ ID NO:34)

AtTLP8-5' (5'-ATGGCTGGTTCGAGAAAAGTGAA-3')
(SEQ ID NO:35)

AtTLP8-3' (5'-TCAAACAGTACAACAAAGCTTGG-3')
(SEQ ID NO:36)

AtTLP9-5' (5'-ATGACGTTCCGAAGTTTACTCCA-3')
(SEQ ID NO:37)

AtTLP9-3' (5'-TTATTCACAGGCAATTCTGGTTT-3')
(SEQ ID NO:38)

AtTLP10-5' (5'-ATGTCGTTTCGAGGCATTGTTCA-3')
(SEQ ID NO:39)

AtTLP10-3' (5'-CTATTCACAAGCAAGCTTGGTGT-3')
(SEQ ID NO:40)

AtTLP11-5' (5'-ATGTCGTTTCTGAGTATTGTTCG-3')
(SEQ ID NO:41)

AtTLP11-3' (5'-TTATTCACATGCCAATTTAGTAT-3')
(SEQ ID NO:42)
```

RT-PCR was then performed using total RNA from-2-week-old *Arabidopsis* seedlings. The total RNA was isolated using the TRIZOL reagent (Invitrogen) according the manufacture's direction. PolyA$^+$-mRNA was isolated using oligo (dT)-coated magnetic beads and the PolyATract system (Promega, Madison, Wis.). First strand cDNA was synthesized from 0.5 μg PolyA$^+$-mRNA using SuperScript II RNase H Reverse Transcriptase (Invitrogen) according to the protocol of the supplier.

The above-described gene-specific primer pairs were used for amplifying cDNA of each AtTLP gene from first-strand cDNA. PCR conditions were as follows: 3 min at 94° C.; 25 cycles of 1 min denaturation at 94° C./1 min annealing at 55° C./1 min 30 s extension at 72° C. The PCR products were purified using the QIAquick PCR purification kit (Qiagen) and subcloned into a T-easy vector (Promega). Each of these clones was verified by sequencing. Ten AtTLP cDNAs, AtTLPs 1-3 and AtTLPs 5-11, were successfully amplified.

It was found that, except for AtTLPs 2 and 11, the amino acid sequences deduced from the cDNA sequences of AtTLPs 1, 3, and 5-10 are identical to the predicted ORFs in the database. The analysis of the AtTLP2 cDNA sequence indicated that its intron3 was located between 708-781 bp whereas the predicted splicing sites for this intron located were 663 and 766 bp. The analysis of AtTLP11 cDNA sequence showed that intron2 and intron4 were located at 669-803 bp and 1334-1575 bp, respectively, whereas the computer predicted intron2 was at 621-803 bp and there was no predicted intron4. All cDNA sequences obtained from this study were submitted to GenBank.

Sequence Analysis of AtTLP Proteins

The search for all known motifs in the deduced AtTLP amino acid sequences was conducted by MOTIF SCANNING (Pagni et al., 2001, Nucleic Acids Res 29: 148-151). Multiple sequence alignment was performed using ClustalW (Thomopson et al., 1994). This analysis reveled that each AtTLP gene, except AtTLPs 4 and 8, had a well-conserved tubby domain at its C-terminus. Unlike animal TLPs, which have highly diverse N-terminal sequences, each AtTLP, except AtTLP8, had a conserved F-box (51-57 residues) containing domain (Pfam PF00646).

Pair-wise comparisons among the AtTLP proteins revealed that their tubby domains shared 30% to 80% similarities. Further analyzing the tubby domain revealed two PROSITE signature patterns: TUB1 (Prosite Accession No. PS01200) and TUB2 motif (Prosite Accession No. PS01201). The TUB1 and TUB2 motifs were located at the C-terminal of each AtTLP protein and contain 14 and 16 amino acid residues, respectively. These two TUB motifs are highly conserved among TLPs from various organisms. Though AtTLP4 and 8 do not have obvious TUB1 and TUB2 motifs, their C-terminal tubby domains are recognizable by MOTIF SCANNING (N-score >15) (Pagni et al., 1993, Nucleic Acids Res 29: 148-151).

An obvious feature of AtTLPs is the tubby domain. In the tubby domain of a mouse TUBBY protein, three positively-charged amino acid residues, R332, R363 and K330, were thought to be crucial for PI (4,5) $P_2$ binding (Santagata et al., 2001, Science 292: 2041-2050). A sequence alignment of AtTLP tubby domains with the mouse TUBBY domain revealed a putative PI (4,5) $P_2$ binding domain in each AtTLP, except AtTLPs 4 and 8. This suggests that AtTLPs 1-3, 4-7, and 8-11 may bind to PI (4,5) $P_2$. It is known that the mouse TUBBY protein is a bipartite transcription regulator. Its tubby domain possesses double-stranded DNA binding activity, and its N-terminal segment seems to modulate transcription (Boggon et al., 1999, Science 286: 2119-2125). In plants, the N-terminal region of TLPs is quite different from that in mammal TLPs as AtTLP9-GAL4 DNA binding domain fusion protein failed to activate transcription from a GAL4 promoter in a heterologous system.

Location and Gene Structure Comparison of the AtTLP Gene Family

Chromosome localizations of each AtTLP genes were determined using Map View available at the website of *arabidopsis*.org/servlets/mapper (Huala et al., 2001, Nucleic Acids Res 29: 102-105). It was found that the genes were not evenly distributed on chromosomes I, II, III, and V. Seven genes (AtTLPs 1, 4, 5, 6, 7, 8, and 10) were located on chromosome I, and two genes (AtTLPs 2 and 3) were located on chromosomes II. The other two, AtTLPs 9 and 11, were located on chromosomes II, III respectively. Although most of the AtTLP genes were located on chromosome I, no local tandem repeats or gene clusters were identified.

By comparing the sequences of the RT-PCR products and the *Arabidopsis* genome, the corrected exon-intron organizations of the AtTLP genes (except for AtTLP4) were determined. It was found that exon 1 contained the sequences encoding each protein's N-terminal leading sequence, the F-box, and a nine-residue spacer between the F-box and tubby domain. This result indicated that the genes might have arisen from the same ancestral gene. The sequence encoding the C-terminal tubby domain was found to distribute in exons interrupted by 2 or 3 introns. On the basis of the exon and intron composition, the AtTLP genes were classified into three groups. Each gene of the first group (AtTLPs 1, 2, 5, 6, 7, and 10) contains three introns. Each of the second group, AtTLPs 3, 9 and 11, contains an additional intron in the region encoding the C-terminal part of the tubby domain. The third and the most distinct group (AtTLPs 4 and 8) contain 5 and 8 introns, respectively.

Expression of AtTLP Genes

A coupled RT-PCR based assay was conducted to determine the expression pattern of AtTLP genes. Total RNA was isolated from roots, main and lateral stems, rosette leaves, flower clusters, and green siliques of 42-days-old soil-grown *Arabidopsis*. For each gene, a pair of gene-specific primers was chosen, and PCR amplifications were carried out using 15 ng of first strand cDNA synthesized as described above. Primers of ubiquitin gene, UBQ10, (5'-ATTTCT-CAAAATCTTAAAAACTT-3' (SEQ ID NO:43) and 5'-TGATAGTTTTCC CAGTCAAC-3' (SEQ ID NO:44)) were used to amplify ubiquitin, which served as an internal loading standard (Norris et al., 1993, Plant Mol. Biol. 21: 895-906).

The results showed that AtTLPs 1, 2, 3, 6, 7, 9, 10 and 11 were expressed in all organs tested, with slight variations in mRNA accumulation. In contrast, AtTLPs 5 and 8 were primarily expressed in the root, flower, and silique. The organ-specific expressions of AtTLPs 5 and 8 indicate their specific roles in particular organs.

Although the expression of AtTLP1, 2, 3, 6, 7, 9, 10 and 11 is present in all tissues tested, the possibility that these genes are expressed with cell type specificity could not be excluded. It is possible that differential expression of these AtTLP genes could only be observed when internal developmental programming was altered or specific environmental stimuli were applied to the plants. To test this hypothesis, the public *Arabidopsis* Functional Genomics Consortium (AFGC) microarray expression database (the Stanford Microarray Database, available at the website of stanford-.edu/MicroArray/SMD/) (Wu et al., 2001, Plant Physiol Biochem 39: 917-926) was searched. Twofold expression was used as the difference cutoff. Based on the search, the expression profiles of DNA fragments corresponding to AtTLP2, 7, 9 and 10 were summarized in Table 2 below.

TABLE 3

Microarray analysis of AtTLP genes expression

| Experiment | Channel 1 Description | Channel 2 Description | Ch2/Ch1 Normalized (Mean)[b,c] | | | |
|---|---|---|---|---|---|---|
| | | | AtTLP2 | AtTLP7 | AtTLP9 | AtTLP10 |
| Hormone Effect | | | | | | |
| Auxin Response | msg seedlings, untreated | msg seedlings, 10 uM IAA for 30 min | 0.32 | 2.21 | | |
| Auxin Induction | Mock-treated Columbia roots | NAA-treated Columbia roots | | 0.46 | | 2.22 |
| Cytokinin response | Control | 15 min cytokinin treatment | 2.19 | | | |
| Abscisic acid Insensitive 1 | Wild type control | Abscisic acid insensitive 1 mutant | 0.49 | 2.6 | 0.35 | |
| edrl Mutant | Wild type leaves | edrl mutant leaves | 2.33 | | | |
| Downstream genes of KN1 | Control | Overexpression of KN1-GR in Columbia-0 background | 0.43 | 2.78 | | 4.73 |
| Stress | | | | | | |
| Effects of Elevated atmospheric $CO_2$ | Columbia leaves 360 ppm $CO_2$ | Columbia leaves 1000 ppm $CO_2$ | 0.33 | | | |
| Genes involved in chilling tolerance | Cold treated Columbia wild type tissue | Cold treated cls8 mutant tissue | 0.22 | | 0.15 | |
| Genes involved in potassium nutrition | [K+] = 120 uM | [K+] = 2 mM | | | 0.34 | 0.2 |
| Cadmium | Control | 10 uM cadmium treated plant | | | 2.72 | |
| Light Signaling | | | | | | |
| Circadian rhythm time = 12.0 | Time = 0 hrs | Time = 12 hrs | 0.37 | | | |
| Phototropic stimulation | Seedlings grown in the dark and exposed to 1 hr blue light | nph4–2 seedlings grown in the dark and exposed to 1 hr blue light | 2.08 | | | |
| Protein import into chloroplasts: CIA-2 | Wild type | cia-2 (mutant) | | | | 3.46 |
| Identification of genes in chlorophyll starvation | WT leaves after exposure to 230 uE for 2 days | cch1 leaves after exposure to 230 uE for 2 days | | | | 2.02 |

TABLE 3-continued

Microarray analysis of AtTLP genes expression

| Experiment | Channel 1 Description | Channel 2 Description | Ch2/Ch1 Normalized (Mean)[b,c] | | | |
|---|---|---|---|---|---|---|
| | | | AtTLP2 | AtTLP7 | AtTLP9 | AtTLP10 |
| Stress | | | | | | |
| Effects of Elevated Atmospheric $CO_2$ | Columbia leaves 360 ppm $CO_2$ | Columbia leaves 1000 ppm $CO_2$ | 0.33 | | | |
| Genes involved In chilling tolerance | Cold treated Columbia wild type tissue | Cold treated cls8 mutant tissue | 0.22 | | 0.15 | |
| Genes involved in potassium nutrition | [K+] = 120 uM | [K+] = 2 mM | | | 0.34 | 0.2 |
| Cadmium | Control | 10 uM cadmium treated plant | | | 2.72 | |

[a]These data are obtained from the website of afgc.stanford.edu/afgc_html/site2.htm
[b]All data are corresponding with fluorescence intensities greater than 500 in both channels and ch2/ch1 normalized ratio ≧2.0 or ≦0.5
[c]When searching dbEST with blastn, we find Arabidopsis EST corresponding to fragments of four AtTLPs represented on microarray data generated by AFGC. AtTLP2 is corresponding to the EST clone 289B10T7 and 173K22T7. AtTLP7 AtTLP9 and AtTLP10 are corresponding to the EST clone 173G1T7, 201E19T7 and F3E6T7, respectively.

The resulted show that factors like hormone fluctuation and environmental stimuli modulate the expression of the four AtTLP genes. As shown in Table 2, the four AtTLP genes had different responses to treatments of various hormones. AtTLP2 gene expression instantaneously increased more than twofold with cytokinin treatment but decreased to one-third after being treated with IAA. This suggests that Cytokinin and auxin play antagonistic roles in regulating AtTLP2 gene expression.

Another cytokinin-related experiment was aimed at identifying downstream genes of KN1. KN1-like protein is a homeobox transcription factor. Its overexpression upregulates cytokinin production and leads to delayed senescence (Vollbrecht et al., 1991, Nature 350: 241-243). The expression of AtTLP7 and 10 is upregulated in KN1 overexpression transgenic plant while AtTLP2 is down-regulated.

The different responses of AtTLPs 7, 2, and 10 to ABA treatment is also worth noticing. In abscisic acid insensitive 1 mutant (Pei et al., 1997, Plant Cell 9: 409-423), the expression of AtTLP2 and AtTLP10 decreases by two to threefold, but AtTLP7 expression increases over twofold. Interestingly, AtTLP2 and AtTLP7 behaved oppositely to auxin treatment and in abscisic acid insensitive 1 mutant and KN1 overexpression transgenic plant. These two AtTLPs therefore may function antagonistically in regulating phytohormone-signaling pathways.

The expression level of AtTLP2 rose in the edr1 (enhanced disease resistance 1) mutant leaves. The EDR1 gene encodes a putative MAP kinase similar to CTR1, a negative regulator of ethylene response in *Arabidopsis* (Frye et al., 2001, Proc. Nat. Acad. Sci. 98: 373-378). The edr1 mutation of *Arabidopsis* also confers resistance to powdery mildew disease (Frye and Innes, 1998, Plant Cell 10: 947-956). Thus, the regulation of AtTLP2 gene expression may be associated with SA-inducible and ethylene defense mechanism.

Environmental stresses also impose influences on the expression of AtTLP genes. For example, similar to the cold treatment on cls8 mutant, elevated $CO_2$ level inhibited the expression of AtTLP2. K+ deficiency augmented the expression of AtTLPs 7 and 10 by threefold and fivefold, respectively. Heavy metal cadmium treatment stimulated the expression of AtTLP9.

In conclusion, the expression data of these four AtTLP genes indicate their involvement in phytohormone and environmental stress signaling.

AtTLP9 Interacts with ASK1 Protein

Homology searches in the public databases reveal that TLPs were also present in multiple plant species, including *Lemna paucicostata, Oryza sativa, Cicer arietinum*, maize, and *Arabidopsis*. Unlike animal TLPs having highly diverse N-terminal sequences, plant TLPs had conserved F-box-containing domain. Sequence alignment of the F-box cores from AtTLP, TIR, UFO, COI1 and the human F-box protein Skp2 revealed conserved islands separated by regions with weak homology. Many of the conserved residues correspond with those known to be important for Skp association (Schulman et al., 2000, Nature 408: 381-386 and Zheng et al., 2002, Nature 416: 703-709).

The F-box domain, first found in cyclin-F, interacts with the protein SKP1, which interacts with the Cdc53 (Cullin) proteins, to form a so-called SCF complex. The F-box is involved in recruiting specific proteins (e.g., transcription activators or repressors) and targeting them for ubiquitin-mediated proteolysis by 26S proteosome. Analysis of the *Arabidopsis* genome revealed that *Arabidopsis* had 21 Skp1-like, or ASK, protein, which exhibited different expression patterns. Among them, ASK1 is involved in vegetative growth and reproductive development (Zhao et al., 2003, Plant Physiology 133: 203-217).

To test whether AtTLP could interact with ASK1, AtTLP9 was examined by the yeast two-hybrid analysis. Yeast two-hybrid vectors, pAD-GAL4-2.1 and pBD-GAL4 Cam (Stratagene, La Jolla, Calif.), were used for C-terminal GAL4 AD and BD fusion constructions, respectively. A 1.1-kb SalI-PstI fragment containing the entire coding region of AtTLP9 was cloned into the SalI-PstI site of the pBD-GAL4 Cam vector. A 480-bp EcoRI-PstI fragment containing the entire coding region of ASK1 (Atg175950) was cloned into the EcoRI-PstI site of the pAD-GAL4-2.1 vector. The yeast strain YRG-2 [MATa ura3-52 his3-200 ade2-101 lys2-801 trp1-901 leu2-3,112 gal4-542 gal80-538 LYS2::GAL1UAS-GAL1TATA-HIS3 URA3::(GAL43× 17mer)-CYC1TATA-lacZ] was co-transformed with the two vectors. The Y2H analysis was performed according to the manufacturer's recommendations (Stratagene). The result suggested that AtTLP9 physically interacts with ASK1 to form SCF complex and acts as a factor for substrate recognition in the ubiquitin-mediated proteolysis.

Attlp9 Null Mutants and Overexpression Lines

ATLP9 was analyzed to investigate for it in vivo functions. Both loss-of-function and overexpression approaches were taken to address its biological roles.

To identify attlp9 T-DNA insertion mutant, AtTLP9 (At3g06380) was used to search the T-DNA Express database at the website of signal.salk.edu/cgi-bin/tdnaexpress. Two attlp9 T-DNA insertion mutants (ABRC seed stock SALK_016678 and 051138) were identified and designated as attlp9-1 and attlp9-2. T3 seeds of attlp9-1 and attlp9-2 were obtained from the *Arabidopsis* Biological Resource Center (Ohio State University, Columbus). The position of the T-DNA within the AtTLP9 gene was re-confirmed by sequencing a PCR-amplified fragment amplified by primer pairs corresponding to the T-DNA left borders and the AtTLP9 gene specific primer. The following primer pairs were used for attlp9-1 and attlp9-2 specific amplification,

```
                                        (SEQ ID NO:45)
    attlp9-1: N1, 5'-ATGACGTTCCGAAGTTTACTC-3';

(SEQ ID NO:46)
    LBa1, 5'-TGGTTCACGTAGTGGGCCATC-3';

(SEQ ID NO:47)
    attlp9-2: C1, 5'-TTATTCACAGGCAATTCTGGT-3';

and
                                        (SEQ ID NO:46)
    LBa1, 5'-TGGTTCACGTAGTGGGCCATC-3'.
```

It was found that Attlp9-1 had a T-DNA insertion in the coding sequence at codon 705, whereas attlp9-2 had an insertion in the 5' distal region of this gene. The T-DNA insertion site of attlp9-1 was identical to that originally described in the T-DNA Express database. However, the T-DNA insertion site of attlp9-2 was in the promoter region instead of exon1 as predicted in the database (the latter is supported by a potential full length cDNA corresponding to At3g06380 generated in RIKEN, accession number BT004092).

Southern blot was conducted with the nptII marker gene to determine the T-DNA insertion number in attlp9-1 and 9-2 knockout mutants. It was found that one and three T-DNA insertion events in the $T_4$ attlp9-1 and attlp9-2 T-DNA insertion mutants, respectively.

The T-DNAs in attlp9-1 and attlp9-2 carried a gene leading to resistance to kanamycin. Homozygous analyses of attlp9-1 and attlp9-2 plants were carried out by kanamycin selection and PCR based method. RT-PCR analyses of $T_4$ homozygous of attlp9-1 and attlp9-2 plants indicated that attlp9-1 was a null allele, whereas attlp9-2 was somewhat leaky. For the phenotype investigation, attlp9-1 and attlp9-2 $T_4$ homozygous lines were used for detailed analysis.

Transgenic plants with overexpressing AtTLP9 were generated. An XbaI-SmaI fragment of AtTLP9 was inserted into an XbaI-SmaI site of the pBI121 Ti-vector (Clontech) to generate a 35S::AtTLP9 sense construct. The XbaI-SmaI fragment contained the entire AtTLP9 coding region and was under the control of the 35S promoter of cauliflower mosaic virus. The constructs were introduced into *Agrobacterium* strain LBA4404 by electroporation and transformed into wild-type plants by the floral dip method (Clough et al., 1998, Plant J 16: 735-743). 38 independent transgenic lines ($T_0$ generation) were obtained. Among them, seven independent homozygous lines from the $T_3$ sense transgenic plants were analyzed for the AtTLP9 expression. Each of these lines contained a single copy of the transgene. Two independent transgenic lines (S13-2 and S16-1) showed dramatic increases in the AtTLP9 transcript levels and were further analyzed. A number of control transgenic lines were generated by transforming with *Agrobacterium* with PBI121 vector alone.

The wild type *Arabidopsis thaliana* ecotype Columbia-0 (Col-0) and mutant abi4-1 (obtained from Dr Wan-Hsing Cheng, Institute of Botany, Academia Sinica Taipei) were used. The phenotypes of abi4-1 were confirmed as described (Söderman et al., 2000, Plant Physiol. 124: 1752-1765) prior to use.

All seeds of the above-described lines were surface sterilized with 70% ethanol for 30 s and then with 6% household bleach for 5 min before being washed five times with sterile water. For aseptic growth, they were plated on solid medium containing Murashige and Skoog salts (Invitrogen), vitamins (Duchefa), 0.7% phytoagar (Invitrogen), and 1% sucrose and transferred to a tissue culture room. For soil growth, seedlings were transferred into individual pots 8-10 days after germination and maintained in the growth chamber. Plants were grown at 22° C. under a 16-hr-light/8-hr-dark photoperiod aseptically or on soil.

The general development and growth phenotypes of the attlp9-1 and attlp9-2 knockout plants appear to be similar to those of the wild type plants. However, when seeds were plated on nutrient agar media, the germination time of mutant attlp9-1 and attlp9-2 seeds was advanced several hours compared with that of the wild type plants, whereas the selected sense line seeds (i.e., S13-2 and S16-1) germinated later than vector control seeds. It was found that 50% of the wild type seeds geminated after about 37 hour after plating. In contrast, 50% of the attlp9-1 and attlp9-2 knockout seeds geminated at hours 26-28 after plating, and 50% of the S13-2 and S16-1 seeds geminated around hours 40-42 hours after plating.

Effect of ABA on Seed Germination of Attlp9 Mutants and Overexpression Lines

It is known that seed germination is the outcome of an integration of many signals coordinated by the interactions of stage-specific developmental regulators and the competing effects of hormonal signals (Finkelstein et al., 2002, Curr. Opin. Plant. Biol. 5: 26-32). The most critical hormone promoting embryo maturation and preventing germination is ABA.

To determine whether the transgenic plants display altered ABA responses, the above-described lines were germinated on media containing various concentrations of ABA. Seeds collected at the same or similar times were used. After surface-sterilization, sterile seeds were suspended in 0.15% agarose, and kept in the dark at 4° C. for 3 days to break residual dormancy. The seeds were then plated on agar plates in six replicates containing no ABA or 0.25, 0.5, 0.75, or 1.0 µM ABA in 12-cm plastic petri dishes. Each agar plate was divided into seven sections, and 50 seeds of WT and AtTLP9 transgenic seeds were plated on each section. A seed was regarded as germinated when the radicle protruded through the seed coat.

In the presence of 1 µM ABA, the germination of sense lines seeds was further delayed and the germination rate was reduced to less than 10%. In contrast, the germination rate of attlp9-1 and attlp9-2 mutant seeds nearly reached 50%, and about 30% of wild-type seeds were able to germinate in the presence of 1 µM ABA. These results suggest that the disruption of the AtTLP9 gene affects the sensitivity of seeds to exogenous ABA.

In addition to reducing seed germination rate, ABA also inhibited the growth and the greening process in cotyledons of the sense transgenic lines. In MS agar medium containing 1 µM ABA and 1% sucrose, 90% of the 10-d-old seedlings showed developmental arrest although the radicles of most sense lines seeds emerged. In contrast, under the same conditions, attlp9-1 and attlp9-2 plants continued to grow and about 45% of the seedlings continued to develop true leaves, although at slower rates than abi4-1 mutant does. These results indicate that the alteration of AtTLP9 modulate plant's sensitivity to ABA during seed germination and early seedling development.

AtTLP9 Expression is Transiently Up-regulated During Imbibition of Seeds

Real-time PCR experiments were conducted to quantify AtTLP9 transcript levels at seed maturation, seed germination, and early development stage. UBQ10 was used as the endogenous control (Norris et al., 1993, Plant. Mol. Biol. 21: 895-906). Primers were designed using Primer Express 1.0 software (Applied Biosystems). The primers used were:

```
AtTLP9 forward primer,          (SEQ ID NO:48)
5'-TAGGCCACACCGTGTAGTTCA-3';

AtTLP9 reverse primer,          (SEQ ID NO:49)
5'-CGTCAACAGTCTCAACCCTAATCA-3';

UBQ10 forward primer,           (SEQ ID NO:50)
5'-AGAAGTTCAATGTTTCGTTTCATGTAA-3'; and UBQ10 reverse primer,           (SEO ID NO:51)
5'-GAACGGAAACATAGTAGAACACTTATTCA-3'.
```

The real-time PCR was performed in a 50 µL reaction mixture containing 500 ng first strand cDNA, 2.5 µM each primers and 1× SYBR Green PCR Master Mix (Applied Biosystems). PCR cycling was 50° C. for 2 min, 95° C. for 10 min, followed by 40 cycles of 15 sec at 95° C./1 min at 60° C. The UBQ10 mRNA quantity was set at '1' and AtTLP9 expression was determined relative to control samples. Threshold cycles were determined by Sequence Detection System V. 1.7a software (Applied Biosystems). The products were quantified by the ABI PRISM 7700 Sequence Detection System (Applied Biosystems, Scoresby, Victoria, Australia).

Seed germination is divided into three phases: imbibition, increased metabolic activity, and initiation of growth (Bewley. 1997, Plant Cell 9: 1055-1066). It was found that during seed maturation and seed imbibition at 4° C. for 72 h, AtTLP9 transcripts remained at a relatively low level. When the seeds were transferred to 22° C. for further incubation, the levels rose after 8 h, peaked at 16 h, and fell rapidly after 24 h when the radicle emerged. The AtTLP9 transcripts were barely detectable afterwards. The transient expression of AtTLP9 indicated that AtTLP9 functions at stage II of seed germination as a checkpoint before radicle protrusion.

OTHER EMBODIMENTS

All of the features disclosed in this specification may be combined in any combination.

Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the scope of the following claims.

What is claimed is:

1. A transformed plant cell comprising a recombinant nucleic acid that encodes the heterologous polypeptide of SEQ ID NO: 9.

2. A transgenic plant comprising a recombinant nucleic acid that encodes the heterologous polypeptide of SEQ ID NO: 9.

3. A method of producing a transformed plant cell, the method comprising:
   introducing into a plant cell a recombinant nucleic acid encoding the heterologous polypeptide of SEQ ID NO: 9, and
   expressing the polypeptide in the cell.

4. A method of producing a transgenic plant, the method comprising:

introducing into a plant cell a recombinant nucleic acid encoding the heterologous polypeptide of SEQ ID NO:9, expressing the polypeptide in the cell, and cultivating the cell to regenerate a plant.

5. A transformed plant cell comprising a heterologous DNA sequence that encodes a polypeptide having at least 95% sequence identity to SEQ ID NO:9, and wherein expression of the DNA sequence in said plant cell confers increased sensitivity to ABA relative to an untransformed plant cell of the same species.

6. A method of producing a transformed plant cell, the method comprising introducing into a plant cell a heterologous DNA sequence that encodes a polypeptide having at least 95% sequence identity to SEQ ID NO:9, and wherein expression of the DNA sequence in said plant cell confers increased sensitivity to ABA relative to an untransformed plant cell of the same species.

7. A method of producing a transgenic plant, the method comprising introducing into a plant cell a heterologous DNA sequence that encodes a polypeptide having at least 95% sequence identity to SEQ ID NO:9, and cultivating the transformed cell to regenerate the transgenic plant, wherein expression of the DNA sequence in said plant confers increased sensitivity to ABA relative to an untransformed plant of the same species.

* * * * *